(12) United States Patent
Parker

(10) Patent No.: US 11,243,205 B2
(45) Date of Patent: Feb. 8, 2022

(54) METHOD OF DIAGNOSIS OF BREAST CANCER

(71) Applicant: LA TROBE UNIVERSITY, Victoria (AU)

(72) Inventor: Belinda Sheree Parker, Alphington (AU)

(73) Assignee: Peter MacCallum Cancer Institute, Melbourne (AU)

( * ) Notice: Subject to any disclaimer, the term of this patent is extended or adjusted under 35 U.S.C. 154(b) by 522 days.

(21) Appl. No.: 15/574,903

(22) PCT Filed: May 20, 2016

(86) PCT No.: PCT/AU2016/050392
§ 371 (c)(1),
(2) Date: Nov. 17, 2017

(87) PCT Pub. No.: WO2016/187656
PCT Pub. Date: Dec. 1, 2016

(65) Prior Publication Data
US 2018/0275128 A1 Sep. 27, 2018

(30) Foreign Application Priority Data

May 22, 2015 (AU) .................................. 2015901895

(51) Int. Cl.
*G01N 33/574* (2006.01)
*A61K 38/21* (2006.01)
*C12Q 1/6886* (2018.01)

(52) U.S. Cl.
CPC ..... *G01N 33/57415* (2013.01); *C12Q 1/6886* (2013.01); *C12Q 2600/118* (2013.01); *G01N 2333/4703* (2013.01); *G01N 2333/70596* (2013.01); *G01N 2800/52* (2013.01)

(58) Field of Classification Search
CPC ..... G01N 33/57415; G01N 2333/4703; G01N 2333/70596; G01N 2800/52; C12Q 1/6886; C12Q 2600/118
See application file for complete search history.

(56) References Cited

U.S. PATENT DOCUMENTS

2013/0156790 A1* 6/2013 Zitvogel .................. A61N 5/10
424/158.1

FOREIGN PATENT DOCUMENTS

| WO | 2014012147 A1 | 1/2014 |
| WO | 2014074785 A1 | 5/2014 |
| WO | 2015026634 A1 | 2/2015 |

OTHER PUBLICATIONS

Soliman et al, Cancer Res, 74:A5018, 2014.*
Kaur et al, BMC Cancer, 12:120. 2012.*
Zhao, Cancer Biother Radiopharm, 27:530-534, 2012.*
Potu et al, Cancer Res, 70:655-665, 2010.*
Abramson et al., "Subtyping of triple-negative breast cancer: implications for therapy", Cancer. 2015;121(1):8-16.
Alon et al., "Broad patterns of gene expression revealed by clustering analysis of tumor and normal colon tissues probed by oligonucleotide arrays", Proc. Natl. Acad. Sci. USA: 96,6745-76750, Jun. 1999.
Andrews et al., "Recognition of H2-M3 by Ly49A regulates natural killer cell licensing and activation", Nature immunology. 2012;13(12):1171-7.
Bidwell et al., "Silencing of Irf7 pathways in breast cancer cells promotes bone metastasis through immune escape", Nature medicine. 2012;18(8):1224-31.
Boch , "TALEs of genome targeting", Nature biotechnology. 2011;29(2):135-6.
Bunin et al., "The combinatorial synthesis and chemical and biological evaluation of a 1,4-benzodiazepine library", Proc. Natl. Acad. Sci. USA, (1994) 91:4708-4712.
Cao et al., "BMP4 inhibits breast cancer metastasis by blocking myeloid-derived suppressor cell activity", Cancer research. 2014;74(18):5091-102.
Chan et al., "The receptors CD96 and CD226 oppose each other in the regulation of natural killer cell functions", Nature immunology. 2014;15(5):431-8.
Chen et al., "Kinetic polymerase chain reaction on pooled DNA: A high-throughput, high-efficiency alternative in genetic epidemiological studies", Genome Res. 10:258-266 (2000).
De Kruijf et al., "NKG2D ligand tumor expression and association with clinical outcome in early breast cancer patients: an observational study", BMC cancer. 2012;12:24.
Demaria et al., "Development of tumor-infiltrating lymphocytes in breast cancer after neoadjuvant paclitaxel chemotherapy", Clinical cancer research. 2001;7(10):3025-30.
Derisi et al., "Use of a cDNA microarray to analyse gene expression patterns in human cancer", Nature Genetics 14:457-460 (1996).
Dewitt et al., ""Diversomers": An approach to nonpeptide, nonoligomeric chemical diversity", Proc. Natl. Acad. Sci. USA, (1993) 90:6909-6913.
Eckhardt et al., "Genomic analysis of a spontaneous model of breast cancer metastasis to bone reveals a role for the extracellular matrix. Molecular cancer research", MCR. 2005;3(1):1-13.

(Continued)

*Primary Examiner* — Mark Halvorson
(74) *Attorney, Agent, or Firm* — Kilpatrick Townsend & Stockton LLP

(57) ABSTRACT

The present invention relates generally to a method of prognosing the survival of a patient with a breast neoplasm, more particularly a patient with a breast neoplasm which is estrogen receptor-/progesterone receptor-/HER-2-("triple-negative"). The method of the present invention more particularly provides a method for prognosing breast cancer patient survival, in particular risk of metastatic spread, by screening for IRF9 expression. In a related aspect, the present invention provides a method of therapeutically or prophylactically treating patients with a triple-negative breast neoplasm, in particular those patients with triple-negative breast neoplasia which is characterised by a poor survival prognosis, still more particularly a high risk of metastatic spread, by upregulating type I IFN levels.

18 Claims, 12 Drawing Sheets

Specification includes a Sequence Listing.

(56) References Cited

OTHER PUBLICATIONS

Egleton et al., "Bioavailability and transport of peptides and peptide drugs into the brain", Peptides (1997) 18:1431-1439.
Fix, "Oral controlled release technology for peptides: Status and future prospects", Pharm Res. (1996) 13:1760 1764.
Guo et al., "Direct fluorescence analysis of genetic polymorphisms by hybridization with oligonucleotide arrays on glass supports", Nucleic Acids Res. 22:5456-5465 (1994).
Heid et al., "Genome Methods: Real Time Quantitative PCR", Genome Res. 6:986-994 (1996).
Jia et al., "Levels of lymphocyte subsets in peripheral blood prior treatment are associated with aggressive breast cancer phenotypes or subtypes", Medical oncology. 2014;31(6):981.
Ladoire et al., "In situ immune response after neoadjuvant chemotherapy for breast cancer predicts survival", The Journal of pathology. 2011;224(3):389-400.
Ladoire et al., "Pathologic complete response to neoadjuvant chemotherapy of breast carcinoma is associated with the disappearance of tumor-infiltrating Foxp3+ regulatory T cells", Clinical cancer research. 2008;14(8):2413-20.
Langer, "New Methods of Drug Delivery", Science (1990) 249:1527-1533.
Maskos et al., "Oligonucleotide hybridisations on glass supports: a novel linker for oligonucleotide synthesis and hybridisation properties of oligonucleotides synthesised in situ", Nuc. Acids Res. 20:1679-84, 1992.
Moore et al., "Measuring transferrin receptor gene expression by NMR imaging", BBA, 1402:239-249, 1988.
Nagalla et al., "Interactions between immunity, proliferation and molecular subtype in breast cancer prognosis", Genome biology. 2013;14(4):R34.
Neri et al., "Calcein-acetyoxymethyl cytotoxicity assay: standardization of a method allowing additional analyses on recovered effector cells and supernatants", Clin Diagn Lab Immunol. 2001;8(6):1131-5.
Patton, "Breathing life into protein drugs: Inhalation of therapeutic macromolecules is a feasible, natural, more people-friendly, delivery system", Biotechniques (1998) 16:141-143.
Pease, "Light-generated oligonucleotide arrays for rapid DNA sequence analysis", Proc. Natl. Acad. Sci. USA 91(11):5022-5026 (1994).
Putney et al., "Improving protein therapeutics with sustained-release formulations", Nat. Biotechnol. (1998) 16:153 157.
Rouzier et al., "Breast cancer molecular subtypes respond differently to preoperative chemotherapy", Clinical cancer research. 2005;11(16):5678-85.
Samanen et al., "Chemical approached to improve the oral bioavailability of peptidergic molecules", (1996) J. Pharm. Pharmacol. 48:119 135.
Smith et al., "Direct Mechanical Measurements of the Elasticity of Single DNA Molecules by Using Magnetic Beads", Science 258:1122-1126 (1992).
Urdea et al., "Branched DNA amplification multimers for the sensitive, direct detection of human hepatitis viruses", Nucleic Acids Symp. Ser., 24:197-200 (1991).
Wedemeyer et al., "Flow cytometric quanitification of competitive reverse transcription—PCR products", Clinical Chemistry 48:9 1398-1405, 2002.
Weissleder et al., "In vivo magnetic resonance imaging of transgene expression", Nature Medicine 6:351-355, 2000.
Withana et al., "Cathepsin B inhibition limits bone metastasis in breast cancer", Cancer research. 2012;72(5):1199-209.
Yan et al., "Recruitment of regulatory T cells is correlated with hypoxia-induced CXCR4 expression, and is associated with poor prognosis in basal-like breast cancers", Breast cancer research : BCR. 2011;13(2):R47.
International Application No. PCT/AU2016/050392, International Search Report and Written Opinion dated Aug. 5, 2016.
Rachakatla, Raja Shekar, et al. "Combination treatment of human umbilical cord matrix stem cell-based interferon-beta gene therapy and 5-fluorouracil significantly reduces growth of metastatic human breast cancer in SCID mouse lungs." Cancer Investigation 26 (7): 662-670 (2008).
Luker, Kathryn E., et al. "Overexpression of IRF9 confers resistance to antimicrotubule agents in breast cancer cells." Cancer research 61(17): 6540-6547 (2001).
Nanda, Rita, et al. "Pembrolizumab in patients with advanced triple-negative breast cancer: phase Ib KEYNOTE-012 study." Journal of Clinical Oncology 34(21): 2460-2467 (2016).
European Patent Application No. 16798946.6, Extended European Search Report dated Nov. 9, 2018, 8 pages.
Rakha et al., Prognostic Markers in Triple-Negative Breast Cancer, American Cancer Society, vol. 109, No. 1, Jan. 1, 2007, pp. 25-32.
Japanese Patent Application No. 2017-560764, "Office Action", dated Dec. 16, 2020, 7 pages.
Singh, et al., "Curcumin Improves the Therapeutic Efficacy of Listeriaat-Mage-B Vaccine in Correlation with Improved T-Cell Responses in Blood of a Triple-Negative Breast Cancer Model 4t1", Cancer Medicine, vol. 2, No. 4, Aug. 2013, pp. 571-582.
Sitia, et al., "An Integrated Approach for the Systematic Evaluation of Polymeric Nanoparticles in Healthy and Diseased Organisms", Journal of Nanoparticle Research, vol. 16, No. 2481, 2014, pp. 1-16.

* cited by examiner

P=0.0315
HR- 0.435 (95% CI 0.199-0.961)

A)

B)

SEQUENCE LISTING

```
<160> NUMBER OF SEQ ID NOS: 2

<210> SEQ ID NO 1
<211> LENGTH: 54
<212> TYPE: DNA
<213> ORGANISM: Mus musculus

<400> SEQUENCE: 1
gcaagcaaga cttccgaggc aagcaagact tccgaggcaa gcaagacttc cgag      54

<210> SEQ ID NO 2
<211> LENGTH: 35
<212> TYPE: DNA
<213> ORGANISM: Mus musculus

<400> SEQUENCE: 2
gcaagcaagt aggcaagcaa cgaggcactt ccgag      35
```

METHOD OF DIAGNOSIS OF BREAST CANCER

REFERENCE TO SUBMISSION OF A SEQUENCE LISTING AS A TEXT FILE

The ASCII formatted Sequence Listing written in file 1068087_2nd_Sub_SequenceListing.txt created on Jun. 15, 2018, having a size of 525 bytes, is part of the specification and is hereby incorporated by reference in its entirety for all purposes.

FIELD OF THE INVENTION

The present invention relates generally to a method of prognosing the survival of a patient with a breast neoplasm, more particularly a patient with a breast neoplasm which is estrogen receptor/progesterone receptor⁻/HER-2⁻ ("triple-negative"). The method of the present invention more particularly provides a method for prognosing breast cancer patient survival, in particular risk of metastatic spread, by screening for IRF9 expression. In a related aspect, the present invention provides a method of therapeutically or prophylactically treating patients with a triple-negative breast neoplasm, in particular those patients with triple-negative breast neoplasia which is characterised by a poor survival prognosis, still more particularly a high risk of metastatic spread, by upregulating type I IFN levels.

BACKGROUND OF THE INVENTION

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

A neoplasm is an abnormal mass or colony of cells produced by a relatively autonomous new growth of tissue. Most neoplasms arise from the clonal expansion of a single cell that has undergone neoplastic transformation. The transformation of a normal cell to a neoplastic cell can be caused by a chemical, physical, or biological agent (or event) that alters the cell genome. Neoplastic cells are characterized by the loss of some specialized functions and the acquisition of new biological properties, foremost, the property of relatively autonomous growth. They pass on their heritable biological characteristics to progeny cells. Neoplasms may originate in almost any tissue containing cells capable of mitotic division.

The past, present, and future predicted biological behaviour, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm, however, exhibits a lesser degree of autonomy, is usually not invasive and does not metastasize.

Breast cancer will directly impact 1 in 8 women in Australia in their lifetime. Approximately 15% of breast cancer patients will develop spread (metastasis) to distant organs such as lung and bone. Due to the fact that distant metastasis is almost incurable, breast cancer remains the second leading cause of cancer-related death in women. One of the most aggressive subtypes of breast cancer is "basal-like" breast cancer, accounting for up to 15% of cases. Most basal-like breast cancers are "triple-negative" meaning that they do not express the estrogen and progesterone receptors nor do they express the human epidermal growth factor receptor (HER)-2. This is important clinically as it means that patients with triple-negative basal-like cancers will not benefit from anti-estrogen or HER2-targeted therapeutics that are used for other subtypes that express these proteins. In fact, treatment options for patients with triple-negative breast cancer are very limited and untargeted, with only some patients responding well to chemotherapy. Compared to luminal (ER positive) breast cancers, basal-like breast cancers occur in younger women and are associated with a higher risk of rapid metastasis and death 1-5 years after diagnosis. For these reasons, it is essential to understand the biology of basal-like breast cancers, including developing new biomarkers to predict disease spread in patients with this subtype and developing novel targeted therapies to ultimately reduce patient mortality.

Triple-negative breast cancer is considered to be a heterogeneous subtype (Abramson V G, Lehmann B D, Ballinger T J, Pietenpol J A. *Subtyping of triple-negative breast cancer: implications for therapy.* Cancer. 2015; 121(1):8-16) that to date has been difficult to stratify into good and poor outcome groups. Some triple-negative breast cancer patients respond well to chemotherapeutic agents, although this is a minority of patients who cannot be identified in advance. (Rouzier R, Perou C M, Symmans W F, Ibrahim N, Cristofanilli M, Anderson K, et al. *Breast cancer molecular subtypes respond differently to preoperative chemotherapy.* Clinical cancer research. 2005; 11(16):5678-85). However, of the non- or partial responders, the risk of distant relapse is greater than in other subtypes. Importantly, proliferative indices alone do not predict complete response and there are currently no other reliable predictive markers of chemotherapeutic response. Additionally, robust biomarkers that predict disease recurrence and breast cancer-related death in patients with triple-negative breast cancer are lacking. However, the association of tumour infiltrating lymphocytes with both chemotherapeutic sensitivity and disease relapse has been reported by a number of groups (Demaria S, Volm M D, Shapiro R L, Yee H T, Oratz R, Formenti S C, et al. *Development of tumor-infiltrating lymphocytes in breast cancer after neoadjuvant paclitaxel chemotherapy.* Clinical cancer research. 2001; 7(10):3025-30; Ladoire S, Arnould L, Apetoh L, Coudert B, Martin F, Chauffert B, et al. *Pathologic complete response to neoadjuvant chemotherapy of breast carcinoma is associated with the disappearance of tumor-infiltrating foxp3+ regulatory T cells.* Clinical cancer research. 2008; 14(8):2413-20), suggesting that the anti-tumour immune response is an important component of response to chemotherapeutics and triple-negative breast cancer progression. Further studies dissecting the nature of the lymphocytic infiltrate have confirmed that triple-negative breast cancers have increased NK and CD8⁺ T cell infiltrates compared to other breast cancer subtypes (Jia Y, Xu L, Lin Q, Zhu M, Ding L, Wu K, et al. *Levels of lymphocyte subsets in peripheral blood prior treatment are associated with aggressive breast cancer phenotypes or subtypes.* Medical oncology. 2014; 31(6):981). The recruitment of regulatory T-cells is associated with poor prognosis in basal-like breast cancers (Ladoire S, Mignot G, Dabakuyo S, Arnould L, Apetoh L, Rebe C, et al. *In situ immune response after neoadjuvant chemotherapy for breast cancer*

*predicts survival*. The Journal of pathology. 2011; 224(3): 389-400; Yan M, Jene N, Byrne D, Millar E K, O'Toole S A, McNeil C M, et al. *Recruitment of regulatory T cells is correlated with hypoxia-induced CXCR4 expression, and is associated with poor prognosis in basal-like breast cancers*. Breast cancer research BCR. 2011; 13(2):R47). The association between increased expression of an immune module, increased response to chemotherapeutics and decreased risk of metastasis in highly triple-negative breast cancer has also been reported by others (Nagalla S, Chou J W, Willingham M C, Ruiz J, Vaughn J P, Dubey P, et al. *Interactions between immunity, proliferation and molecular subtype in breast cancer prognosis*. Genome biology. 2013; 14(4):R34.

Still further, it has been shown that secretion of type I IFN from tumour cells activates tumour immune surveillance mechanisms that control metastatic spread in cancer. In this regard, two regulators of type I IFN signalling have been shown to be the IFN regulatory factors IRF7 and IRF9 and downregulation in a tumour of the level of expression of genes which comprise an IRF7 binding site or IRF9 has been shown to be indicative of the transition of a primary tumour to a metastatic phenotype. Nevertheless, little is known about the key characteristics of a primary tumour that promote an immune suppressed or activated state nor is it known what mechanisms are at play to regulate metastatic spread subsequent to tumour cell dissemination beyond the primary tumour site, which factors are relevant to the issue of patient survival.

In work leading up to the present invention it has been unexpectedly determined that whereas IRF7 and IRF9 expression have been shown to be indicative of the transition of a primary tumour to a metastatic phenotype, in the context of a specific subpopulation of breast cancer cells, specifically the triple-negative breast cancer cell type, the expression level of IRF9 is prognostic of patient survival and therapeutic responsiveness. The issue of likely patient survival is a significantly more complex one than whether or not metastatic transition, per se, of a primary tumour has, or is likely, to occur. When considering survival, issues such as rate of growth of the neoplastic cells, increase in the number of cell divisions, decrease in the length of the period of cell division, increase in frequency of periods of cell division, evasion of apoptosis, time to onset of metastatic transition and rate of metastatic spread are also highly relevant. To date, however, predicting these factors has been virtually impossible and therefore prognosing likelihood of survival, at an early stage, has been little more than a guess. In relation to triple-negative breast cancers, these are regarded as an aggressive cancer which is difficult to treat and therefore patients are generally regarded as exhibiting poor prognostic outcomes. Accordingly, the determination that, in fact, it is possible to prognose, with a high level of accuracy, likely patient survival, in particular the risk of distant metastatic spread, is both unexpected and extremely valuable. Still further, it has been determined that such a survival prognostic indication is not similarly true of other breast cancer types.

In a related aspect it has also been determined that the triple-negative breast cancer subpopulation, which has to date been regarded as very difficult to treat, is in fact treatable, even where the IRF9-determined prognosis is poor. Specifically, by upregulating Type I IFN expression, prolonged survival can be achieved. Accordingly, this has enabled not only the development of a method of treating triple-negative breast cancer but, also, a means to identify those cancers that should be treated and, just as importantly, those cancers which are either untreatable or else exhibit a good prognosis thereby enabling these patients to make an informed choice not to be treated.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method of prognosing the survival of a patient with a triple-negative breast neoplasm, said method comprising screening said neoplasm for the expression level of IRF9 wherein a lower level of expression of IRF9 relative to the median level expressed by a corresponding neoplasm cohort is indicative of a poor survival prognosis and a level of expression of IRF9 at or above said median level is indicative of a prolonged survival prognosis.

In a related aspect the present invention is directed to a method of prognosing risk of metastatic spread in a patient with a triple-negative breast neoplasm, said method comprising screening said neoplasm for the expression level of IRF9 wherein a lower level of expression of IRF9 relative to the median level expressed in a corresponding neoplasm cohort is indicative of an increased risk of metastatic spread and a level of expression of IRF9 at or above the median level expressed in a corresponding neoplasm cohort is indicative of a low risk of metastatic spread.

In a further aspect the present invention is directed to a method of prognosing risk of metastatic spread in a patient with a triple-negative breast neoplasm, said method comprising screening said neoplasm for the expression level of IRF9 protein wherein a lower level of expression of IRF9 protein relative to the median level expressed in a corresponding neoplasm cohort is indicative of an increased risk of metastatic spread and a level of expression of IRF9 protein at or above the median level expressed in a corresponding neoplasm cohort is indicative of a low risk of said metastatic spread.

In still another aspect the present invention is directed to a method of prognosing risk of metastatic spread in a patient with a triple-negative breast neoplasm, said method comprising screening said neoplasm for the expression level of IRF9 mRNA or cDNA wherein a lower level of expression of IRF9 mRNA or cDNA relative to the median level expressed in a corresponding neoplasm cohort is indicative of an increased risk of metastatic spread and a level of expression of IRF9 mRNA or cDNA at or above the median level expressed in a corresponding neoplasm cohort is indicative of a low risk of said metastatic spread.

In yet another aspect of the present invention is directed to a method of treating a triple-negative breast neoplasia in an individual, said method comprising administering an effective amount of a composition, wherein said composition comprises an agent which upregulates the level of Type I IFN in said individual.

In one embodiment, said neoplasia is characterised by a prognosis of an increased risk of metastatic spread.

In another embodiment said neoplasia is characterised by a poor survival prognosis.

In another further aspect there is provided a method of treating a triple-negative breast neoplasm in a patient, said method comprising administering an effective amount of a composition, wherein said composition comprises an agent which upregulates the level of IFN-α in said patient.

In yet another aspect there is provided a method of treating a triple-negative breast neoplasm in a patient, said method comprising administering an effective amount of a composition wherein said composition comprises an agent which upregulates the level of IFN-β in said individual.

In a related aspect there is provided the use of an agent which upregulates the level of Type I IFN in the manufacture of a medicament for the treatment of a triple-negative breast neoplasm in an individual.

DETAILED DESCRIPTION OF THE INVENTION

Figure 1:
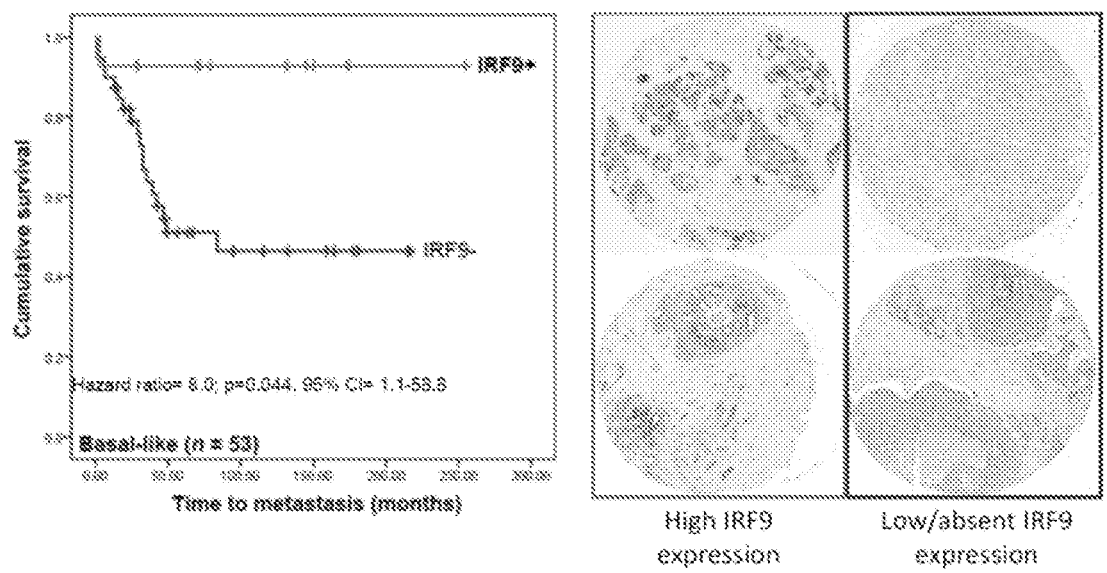
FIG. 1 is an image which depicts that Irf9 protein expression in triple-negative breast cancer predicts decreased risk of distant metastasis and cancer-related death

The present invention is predicated, in part, on the determination that the expression levels of IRF9 are prognostic of the prolonged survival, such as risk of metastatic spread, of a patient with a breast cancer which is estrogen receptor$^-$/progesterone receptor$^-$/HER-2$^-$ (triple-negative). Still further, it has been determined that one can differentiate between those cancers which are likely to be responsive to conventional treatment and those which may not. This finding has therefore facilitated not only the development of a method of screening a patient to determine likely survival outcome but has also enabled the development of a means of rationally treating triple-negative breast cancer patients, in particular those presenting with a poor survival prognosis or with tumours resistant to conventional therapy.

Accordingly, one aspect of the present invention is directed to a method of prognosing the survival of a patient with a triple-negative breast neoplasm, said method comprising screening said neoplasm for the expression level of IRF9 wherein a lower level of expression of IRF9 relative to the median level expressed by a corresponding neoplasm cohort is indicative of a poor survival prognosis and a level of expression of IRF9 at or above said median level is indicative of a prolonged survival prognosis.

Reference to a "neoplastic condition" should be understood as a reference to a condition characterised by the presence or development of encapsulated or unencapsulated growths or aggregates of neoplastic cells. Reference to a "neoplastic cell" should be understood as a reference to a cell exhibiting abnormal growth. Reference to a "neoplasm" should be understood as a reference to a lesion, tumour or other encapsulated or unencapsulated mass or other form of growth or cellular aggregate which comprises neoplastic cells. The term "growth" should be understood in its broadest sense and includes reference to enlargement of neoplastic cell size as well as proliferation.

The phrase "abnormal growth" in this context is intended as a reference to cell growth which, relative to normal cell growth, exhibits one or more of an increase in individual cell size and nuclear/cytoplasmic ratio, an increase in the rate of cell division, an increase in the number of cell divisions, a decrease in the length of the period of cell division, an increase in the frequency of periods of cell division or uncontrolled proliferation and evasion of apoptosis. Without limiting the present invention in any way, the common medical meaning of the term "neoplasia" refers to "new cell growth" that results as a loss of responsiveness to normal growth controls, eg. to neoplastic cell growth. Neoplasias include "tumours" which may be benign, pre-malignant or malignant. The term "neoplasm" should be understood as a reference to a lesion, tumour or other encapsulated or unencapsulated mass or other form of growth or cellular aggregate which comprises neoplastic cells.

The term "neoplasm", in the context of the present invention should be understood to include reference to all types of cancerous growths or oncogenic processes, metastatic tissues or malignantly transformed cells, tissues or organs irrespective of histopathologic type or state of invasiveness.

The term "carcinoma" is recognised by those skilled in the art and refers to malignancies of epithelial or endocrine tissues. Exemplary carcinomas include those forming from tissue of the breast. The term also includes carcinosarcomas, e.g. which include malignant tumours composed of carcinomatous and sarcomatous tissues. An "adenocarcinoma" refers to a carcinoma derived from glandular tissue or in which the tumour cells form recognisable glandular structures.

Neoplasms may be identified, monitored or assessed through clinical screening or diagnostic procedures, including, but not limited to, palpation, biopsy, cell proliferation index, mammography, digital mammography, ultrasonography, computed tomography (CT), magnetic resonance imaging (MRI), positron emission tomography (PET), radiography, radionuclide evaluation, CT- or MRI-guided aspiration cytology, and imaging-guided needle biopsy, among others. Such diagnostic techniques are well known to those skilled in the art.

In another embodiment, said neoplasm is a primary tumour.

Reference to a "triple-negative" breast cancer should be understood as reference to a breast cancer negative for the expression of each of the estrogen receptor, progesterone receptor and HER-2 protein. The main characteristics of triple-negative cancers that have emerged from the literature illustrate their similarities to basal-like cancers, including the fact that they more frequently affect younger patients (<50 years), often present as interval cancers, and are significantly more aggressive than tumours of other subtypes. This aggressiveness is best exemplified by the fact that the peak risk of recurrence is between the first and third years and the majority of deaths occur in the first 5 years following therapy. Patients with triple-negative breast cancers, have a significantly shorter survival following the first metastatic event when compared with those with non-basal-like/non-triple-negative controls.

Since triple-negative breast cancers are generally regarded as highly aggressive and exhibit a poor prognosis, the determination that, in fact, within this subclassification of cancers there is a further subclass in respect of which the prognosis for survival is good, and which subclass can be easily and accurately identified by reference to the level of expression of IRF9 by the tumour cells, has enabled a level of discrimination which was previously unattainable. Patients can therefore now be more precisely assessed for appropriate treatment, thereby avoiding unnecessarily aggressive treatment protocols for patients who exhibit a good prognosis. To date, the inability to differentiate likely survival has resulted in all triple-negative breast cancers being treated very aggressively and non-specifically.

Reference to "prognosis" should be understood as a reference to predicting the likely survival of a patient. The method of the present invention is directed to differentiating triple-negative tumours into those which may ultimately progress and potentially lead to a poor survival outcome for a patient (i.e. progress to a higher grade/become more aggressive) and those which may not. The present invention is therefore directed to detecting the predisposition of a given neoplasm to progress aggressively or not. These findings provide a means of predicting a likely poor survival outcome and treating a patient accordingly, such as by performing radical surgery in order to remove the potentially aggressive cells. To the extent that a good survival outcome is predicted by the diagnostic method of the present invention, highly invasive and/or toxic treatment may be avoidable. The present invention also provides a useful means for performing ongoing testing of a patient in order to monitor for adverse changes to the nature of the subject neoplasm, which changes, in accordance with the findings disclosed herein, predict a change to likely survival outcome. That is, one may continue to monitor a patient who exhibits a good survival outcome in order to screen for the possibility of a switch to an aggressive state and a poor survival outcome.

In terms of "survival", this should be understood as a reference to years of patient survival after initial diagnosis. The subject survival is "prolonged" if it is for 3 years or more, preferably 4 years and more preferably more than 5 years. Prolonged survival that is "metastatic free" is survival during which metastatic spread does not occur. However, it should be understood that the subject prolonged survival may or may not be metastatic free. For example, survival can be significantly improved if metastatic spread is both reduced in quantum and slowed in terms of the rate of cell division. Without limiting the present invention in any way, remission is understood to mean that the signs and symptoms of the cancer are reduced. In this regard, remission can be partial or complete. In a complete remission, all signs and symptoms of cancer have disappeared. If a patient remains in complete remission for 5 years or more, the patient is often regarded as cured. In terms of the present invention, it should be understood that the prognosis relates to survival and not necessarily cure. Accordingly, a patient who exhibits a good prognostic outcome when tested in accordance with the method of the present invention is not necessarily one whose neoplastic state is fully or partially resolved but may be one whose neoplasm either does not metastasise or, if it does, the process is so delayed that survival beyond 3-5 years is achieved. In these cases, survival outcomes may be still further improved by instituting a treatment regime in order to effect cure or to induce full or partial remission. Where a patient is determined to exhibit a poor prognostic outcome, it is to be expected that appropriate treatment regimes, such as the treatment method disclosed herein, would be rapidly deployed.

In one embodiment, the subject survival outcome is risk of metastatic spread. As detailed hereinbefore, the metastatic spread of a tumour is, in fact, a complex transition when considered in terms of the likely survival outcome of a patient. For example, rate of cell division, evasion of apoptosis, time to onset of transition and rate and distance of spread are all factors relevant to likely survival outcome. In the context of the present invention, a means of prognosing metastatic spread, in particular metastatic spread associated with poor survival outcome, is provided.

Accordingly, in a related aspect the present invention is directed to a method of prognosing risk of metastatic spread in a patient with a triple-negative breast neoplasm, said method comprising screening said neoplasm for the expression level of IRF9 wherein a lower level of expression of IRF9 relative to the median level expressed in a corresponding neoplasm cohort is indicative of an increased risk of metastatic spread and a level of expression of IRF9 at or above the median level expressed in a corresponding neoplasm cohort is indicative of a low risk of metastatic spread.

In one embodiment, said prognosis of a high risk of metastatic spread is indicative of a poor survival outcome for the patient.

Preferably, said poor survival prognosis is for less than 3 years.

Without limiting the present invention to any one theory or mode of action, it should be understood that in one aspect the present invention is directed to prognosing patient survival, of which the transition of the cells in the primary tumour to a metastatic phenotype is just one factor. It would be appreciated that even where a primary tumour may have transitioned to a metastatic phenotype, the issue of prolonged patient survival will still depend on the relative aggressiveness of the phenotype, rate of cell division, the timing and distance of metastatic spread and the like. The method of the present invention enables the determination of the survival of a patient, in particular the metastatic free survival of a patient beyond 3 years.

Reference to the "metastatic spread" of a neoplasm should be understood as a reference to the capacity of the cells of the subject neoplasm to spread from the organ or tissue of origin to another organ or tissue, typically via the lymphatics or the blood circulation. It should also be understood that the subject cells may already have transitioned to a metastatic phenotype, although they may or may not have actually travelled to another organ in the patient in whom the neoplasm has developed. In another example, the tumour cells may not have transitioned to a metastatic phenotype, although the differentiation of a prognosis indicating an "increased risk" of metastatic spread is indicative of the fact that not only is said transition highly likely, but it will also likely be aggressive and rapid. Such an increased risk of metastatic spread is likely to occur within 3 years of initial breast cancer diagnosis. Reference to said metastatic spread being of a "low risk" is intended to mean that said metastatic spread would not be expected to occur within 3 years of diagnosis. In one embodiment, said metastatic spread is of a high risk and occurs within 2 years of initial diagnosis and in another embodiment, within 1 year of initial diagnosis. Whether or not the neoplasm exhibits a metastatic phenotype, however, will not by itself be indicative of the rate of cancer spread, aggressiveness, rate of cell division likelihood of imminent or aggressive transition to a metastatic phenotype and, ultimately, whether patient death will occur.

As detailed hereinbefore, the present invention is predicated on the unexpected determination that the level of expression of the transcription factor IRF9 in triple-negative breast cancer cells is indicative of a patient survival prognosis, this not being true of other breast cancer subtypes. More particularly, risk of metastatic spread can be prognosed. Accordingly, the method of the present invention is uniquely useful to this particular subclass of breast cancers. Without limiting the present invention to any one theory or mode of action, interferon regulatory factors (IRFs) are a family of transcription factors with diverse functions which include host defense, cell cycle regulation, apoptosis, oncogenesis, immune cell development and homeostasis. Currently, there are 10 members of the mammalian IRF family (IRFs 1 to 10), all of which contain a conserved DNA binding domain. The DNA binding domain is located at the amino termini of the IRFs and consists of a five-tryptophan repeat that binds to a specific GAAA genomic sequence that is similar to the IFN-stimulated response element (ISRE). The IRFs become activated via phosphorylation at their carboxyl termini, after which they translocate from the cytoplasm to the nucleus to effect transcription of ISRE-containing genes. The various IRFs differ in cellular localisation, structural properties, an activation-induced stimuli, thus conferring each IRF with unique functions.

Reference to "IRF9" should be understood as a reference to all forms of this gene and variants thereof. As would be appreciated by the person of skill in the art, some genes are known to exhibit allelic variation between individuals or single nucleotide polymorphisms. SNPs encompass insertions and deletions of varying size and simple sequence repeats, such as dinucleotide and trinucleotide repeats. Variants include nucleic acid sequences from the same region sharing at least 90%, 95%, 98%, 99% sequence identity i.e. having one or more deletions, additions, substitutions, inverted sequences etc. relative to the genes described herein. Accordingly, the present invention should be understood to extend to such variants which, in terms of the present diagnostic applications, achieve the same outcome despite the fact that minor genetic variations between the actual nucleic acid sequences may exist between individuals. The present invention should therefore be understood to extend to all forms of DNA which arise from any other mutation, polymorphic or allelic variation.

In terms of the method of the present invention, screening for the "level of expression" of IRF9 may be achieved in a variety of ways including screening for any of the forms of RNA transcribed from this gene or cDNA generated therefrom or the protein expression product. Reference to "screening for the level of RNA transcripts" should be understood as a reference to either screening the RNA directly or screening cDNA transcribed therefrom. Changes to the levels of any of these products is indicative of changes to the expression of the subject gene. As detailed hereinbefore, the level of expression of IRF9 in triple-negative breast neoplasms is prognostic of survival outcome, in particular likely metastatic spread. Accordingly, in samples taken from a patient with a poor prognosis one would expect to observe a reduction in transcription and therefore a loss of mRNA transcripts and encoded IRF9 protein expression product. In patients where the prognosis is good one would expect to observe higher levels of IRF9 expression. Still further, the nucleic acid molecule or protein which is identified and measured may be a whole molecule or a fragment thereof. For example, one may identify only fragments of RNA, depending on how the sample has been processed. Provided that said fragment comprises sufficient sequence to indicate its origin with a particular gene or protein, fragmented molecules are useful in the context of the method of the present invention.

Reference to "nucleic acid molecule" should be understood as a reference to both deoxyribonucleic acid molecules and ribonucleic acid molecules and fragments thereof. The present invention therefore extends to both directly screening for RNA levels in a sample or screening for the complementary cDNA which has been reverse-transcribed from an RNA population of interest. It is well within the skill of the person of skill in the art to design methodology directed to screening for DNA, RNA or protein.

In accordance with the previous aspects, in one embodiment said screening method is directed to screening for IRF9 mRNA or cDNA.

In another embodiment, said screening method is directed to screening for the encoded IRF9 protein expression product.

Accordingly, in one embodiment the present invention is directed to a method of prognosing risk of metastatic spread in a patient with a triple-negative breast neoplasm, said method comprising screening said neoplasm for the expression level of IRF9 protein wherein a lower level of expression of IRF9 protein relative to the median level expressed in a corresponding neoplasm cohort is indicative of an increased risk of metastatic spread and a level of expression of IRF9 protein at or above the median level expressed in a corresponding neoplasm cohort is indicative of a low risk of said metastatic spread.

In still another embodiment the present invention is directed to a method of prognosing risk of metastatic spread in a patient with a triple-negative breast neoplasm, said method comprising screening said neoplasm for the expression level of IRF9 mRNA or cDNA wherein a lower level of expression of IRF9 mRNA or cDNA relative to the median level expressed in a corresponding neoplasm cohort is indicative of an increased risk of metastatic spread and a level of expression of IRF9 mRNA or cDNA at or above the median level expressed in a corresponding neoplasm cohort is indicative of a low risk of said metastatic spread.

One may screen for localisation of IRF9 to the intranuclear region of a neoplasm cell, since this would indicate the successful phosphorylation and thereby signalling of the molecule. Alternatively, one can screen for the intracellular presence of the phosphorylated form of IRF9. Although one can screen for changes to the absolute levels of IRF9, it should be understood that the cellular defect which leads to metastatic transition may be a loss of the functional form of IRF9. In this case, the protein may still be present, albeit not in a functional form.

Without limiting the present invention to any one theory or mode of action, IRF9 functions by undergoing phosphorylation and thereafter translocation from the cytoplasm to the nucleus. Once in the nucleus, IRF9 binds to the gene promoter in order to induce transcription. Non-functional protein is therefore detectable either by screening for the localisation of the protein, with cytoplasmic localisation being indicative of non-functionality, or phosphorylation, wherein a lack of phosphorylation is indicative of non-functionality. This form of testing may be done together with testing for the absolute levels of protein or for the RNA transcripts of said proteins.

The subject gene expression or functional protein levels are measured in the cells of the neoplasm. It would be appreciated by the person of skill in the art that the testing of a tumour will often occur after the tumour has been surgically excised. However, to the extent that surgical excision may not be possible or desirable or to the extent that an immediate result is sought, a biopsy specimen can be harvested either at or immediately after initial diagnosis and the testing can be performed on this specimen.

The results obtained from the neoplasm of the individual in issue are assessed relative to the median level of a corresponding neoplasm cohort. This is the control level. By "corresponding" is meant a neoplasm of the same tissue type as the tumour which is the subject of testing, that is, a triple-negative breast neoplasm. The control level may be a standard result which reflects collective results obtained from individuals other than the mammal in issue. This form of analysis is in fact a preferred method of analysis since it enables the design of kits which require only the collection and analysis of a single biological sample, being the test sample of interest. The standard results which provide the control level may be calculated by any suitable means which would be well known to the person of skill in the art. For example, a population of triple-negative neoplastic breast tissue samples can be assessed in terms of the level of IRF9 gene or protein expression thereby providing a standard median value against which all future test samples are analysed. Said "median level" may be a discrete level or a range.

It should also be understood that the method of the present invention may include screening for one or more additional markers. In this regard, it has been unexpectedly determined that the down regulation in expression of both IRF9 and PD-L1 predicts a 7-fold increase in the risk of metastatic spread and a poor prognostic outcome. Without limiting the present invention to any one theory or mode of action, PD-L1 is also known as programmed death-ligand 1, cluster of differentiation 274 (CD274) and B7 homolog 1 (B7-H1). In tumours, this protein is encoded by the CD274 gene. PD-L1 is a 40 kDa type 1 transmembrane protein that has been speculated to play a major role in suppressing the immune system during particular events such as pregnancy, tissue allografts, autoimmune disease and other disease states such as hepatitis.

Accordingly, in one preferred embodiment of the present invention, said method is directed to screening for a reduction in the level of expression of both IRF9 and PD-L1.

The biological sample which is tested according to the method of the present invention may be tested directly or may require some form of treatment prior to testing. For example, a tissue sample may require homogenisation prior to testing or it may require sectioning for in situ testing of the intracellular localisation of IRF9. Alternatively, a cell sample may require permeabilisation prior to testing. Further, to the extent that the biological sample is not in liquid form, (if such form is required for testing) it may require the addition of a reagent, such as a buffer, to mobilise the sample.

The biological sample may be directly tested or else all or some of the nucleic acid or protein material present in the biological sample may be isolated prior to testing. To this end, it would be appreciated that when screening for changes to the level of expression of IRF9, one may screen for the RNA transcripts themselves or cDNA which has been transcribed therefrom. In yet another example, the sample may be partially purified or otherwise enriched prior to analysis. It is within the scope of the present invention for the target cell population or molecules derived therefrom to be pre-treated prior to testing, for example, inactivation of live virus or being run on a gel. It should also be understood that the biological sample may be freshly harvested or it may have been stored (for example by freezing) prior to testing or otherwise treated prior to testing (such as by undergoing culturing).

The term "individual" or "patient" as used herein includes humans, primates, livestock animals (e.g. horses, cattle, sheep, pigs, donkeys), laboratory test animals (e.g. mice, rats, guinea pigs), companion animals (e.g. dogs, cats) and captive wild animals (e.g. kangaroos, deer, foxes). Preferably the mammal is a human or a laboratory test animal. Even more preferably, the mammal is a human.

It should be understood that the lower level of expression of IRF9 in a triple-negative neoplasm which is prognostic of an increased risk of metastatic spread and a poor survival outcome, may be either a partial reduction in the level of expression of IRF9 relative to control levels or it may be a complete absence of expression. It should also be understood that the degree of reduction in expression may vary between patients. However, the critical issue is that the levels of IRF9 will be reduced relative to its corresponding control.

Means of testing for the subject expressed neoplasm markers in a biological sample can be achieved by any suitable method, which would be well known to the person of skill in the art, such as but not limited to:

(i) In vivo detection.
   Molecular Imaging may be used following administration of imaging probes or reagents capable of disclosing altered expression of IRF9.
   Molecular imaging (Moore et al., *BBA*, 1402:239-249, 1988; Weissleder et al., *Nature Medicine* 6:351-355, 2000) is the in vivo imaging of molecular expression that correlates with the macro-features currently visualized using "classical" diagnostic imaging techniques such as X-Ray, computed tomography (CT), MRI, Positron Emission Tomography (PET) or endoscopy.

(ii) Detection of up-regulation of RNA expression in the cells by Fluorescent In Situ Hybridization (FISH), or in extracts from the cells by technologies such as Quantitative Reverse Transcriptase Polymerase Chain Reaction (QRTPCR) or Flow cytometric qualification of competitive RT-PCR products (Wedemeyer et al., *Clinical Chemistry* 48:9 1398-1405, 2002), RNA sequencing, NextGen sequencing, amplification or the like.

(iii) Assessment of expression profiles of RNA, for example by array technologies (Alon et al., *Proc. Natl. Acad. Sci. USA:* 96, 6745-6750, June 1999). A "microarray" is a linear or multi-dimensional array of preferably discrete regions, each having a defined area, formed on the surface of a solid support. The density of the discrete regions on a microarray is determined by the total numbers of target polynucleotides to be detected on the surface of a single solid phase support. As used herein, a DNA microarray is an array of oligonucleotide probes placed onto a chip or other surfaces used to detect complementary oligonucleotides from a complex nucleic acid mixture. Since the position of each particular group of probes in the array is known, the identities of the target polynucleotides can be determined based on their binding to a particular position in the microarray.

Recent developments in DNA microarray technology make it possible to conduct a large scale assay of a plurality of target nucleic acid molecules on a single solid phase support. U.S. Pat. No. 5,837,832 (Chee et al.) and related patent applications describe immobilizing an array of oligonucleotide probes for hybridization and detection of specific nucleic acid sequences in a sample. Target polynucleotides of interest isolated from a tissue of interest are hybridized to the DNA chip and the specific sequences detected based on the target polynucleotides' preference and degree of hybridization at discrete probe locations. One important use of arrays is in the analysis of differential gene expression, where the profile of expression of genes in different cells or tissues, often a tissue of interest and a control tissue, is compared and any differences in gene expression among the respective tissues are identified. Such information is useful for the identification of the types of genes expressed in a particular tissue type and diagnosis of conditions based on the expression profile.

In one example, RNA from the sample of interest is subjected to reverse transcription to obtain labelled cDNA. See U.S. Pat. No. 6,410,229 (Lockhart et al.) The cDNA is then hybridized to oligonucleotides or cDNAs of known sequence arrayed on a chip or other surface in a known order. In another example, the RNA is isolated from a biological sample and hybridised to a chip on which are anchored cDNA probes. The location of the oligonucleotide to which the labelled cDNA hybridizes provides sequence information on the cDNA, while the amount of labelled hybridized RNA or cDNA provides an estimate of the relative representation of the RNA or cDNA of interest. See Schena, et al. *Science* 270:467-470 (1995). For example, use of a cDNA microarray to analyze gene expression patterns in human cancer is described by DeRisi, et al. (*Nature Genetics* 14:457-460 (1996)).

In a preferred embodiment, nucleic acid probes corresponding to the subject nucleic acids are made. The nucleic acid probes attached to the microarray are designed to be substantially complementary to the nucleic acids of the biological sample such that specific hybridization of the target sequence and the probes of the present invention occurs. This complementarity need not be perfect, in that there may be any number of base pair mismatches that will interfere with hybridization between the target sequence and the single stranded nucleic acids of the present invention. It is expected that the overall homology of the genes at the nucleotide level probably will be about 40% or greater, probably about 60% or greater, and even more probably about 80% or greater; and in addition that there will be corresponding contiguous sequences of about 8-12 nucleotides or longer. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions.

In certain embodiments, the probe can be a chimeric molecule; i.e., can comprise more than one type of base or sugar subunit, and/or the linkages can be of more than one type within the same primer. The probe can comprise a moiety to facilitate hybridization to its target sequence, as are known in the art, for example, intercalators and/or minor groove binders. Variations of the bases, sugars, and internucleoside backbone, as well as the presence of any pendant group on the probe, will be compatible with the ability of the probe to bind, in a sequence-specific fashion, with its target sequence. A large number of structural modifications, are possible within these bounds. Advantageously, the probes according to the present invention may have structural characteristics such that they allow the signal amplification, such structural characteristics being, for example, branched DNA probes as those described by Urdea et al. (*Nucleic Acids Symp. Ser.*, 24:197-200 (1991)) or in the European Patent No. EP-0225,807. Moreover, synthetic methods for preparing the various heterocyclic bases, sugars, nucleosides and nucleotides that form the probe, and preparation of oligonucleotides of specific predetermined sequence, are well-developed and known in the art. A preferred method for oligonucleotide synthesis incorporates the teaching of U.S. Pat. No. 5,419,966.

Multiple probes may be designed for a particular target nucleic acid to account for polymorphism and/or secondary structure in the target nucleic acid, redundancy of data and the like. In some embodiments, where more than one probe per sequence is used, either overlapping probes or probes to different sections of a single target gene are used. That is, two, three, four or more probes, are used to build in a redundancy for a particular target. The probes can be overlapping (i.e. have some sequence in common), or are specific for distinct sequences of a gene. When multiple target polynucleotides are to be detected according to the present invention, each probe or probe group corresponding to a particular target polynucleotide is situated in a discrete area of the microarray.

As will be appreciated by those in the art, nucleic acids can be attached or immobilized to a solid support in a wide variety of ways. By "immobilized" herein is meant the association or binding between the nucleic acid probe and the solid support is sufficient to be stable under the conditions of binding, washing, analysis, and removal. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as streptavidin, to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside. In an additional embodiment, the immobilization to the solid support may be very strong, yet non-covalent. For example, biotinylated oligonucleotides can be made, which bind to surfaces covalently coated with streptavidin, resulting in attachment.

The arrays may be produced according to any convenient methodology, such as preforming the polynucleotide microarray elements and then stably associating them with the surface. Alternatively, the oligonucleotides may be synthesized on the surface, as is known in the art. A number of different array configurations and methods for their production are known to those of skill in the art and disclosed in WO 95/25116 and WO 95/35505 (photolithographic techniques), U.S. Pat. No. 5,445,934 (in situ synthesis by photolithography), U.S. Pat. No. 5,384,261 (in situ synthesis by mechanically directed flow paths); and U.S. Pat. No. 5,700,637 (synthesis by spotting, printing or coupling); the disclosure of which are herein incorporated in their entirety by reference. Another method for coupling DNA to beads uses specific ligands attached to the end of the DNA to link to ligand-binding molecules attached to a bead. Possible ligand-binding partner pairs include biotin-avidin/streptavidin, or various antibody/antigen pairs such as digoxygenin-antidigoxygenin antibody (Smith et al., *Science* 258:1122-1126 (1992)). Covalent chemical attachment of DNA to the support can be accomplished by using standard coupling agents to link the 5'-phosphate on the DNA to coated microspheres through a phosphoamidate bond. Methods for immobilization of oligonucleotides to solid-state substrates are well established. See Pease et al., *Proc. Natl. Acad. Sci. USA* 91(11):5022-5026 (1994). A preferred method of attaching oligonucleotides to solid-state substrates is described by Guo et al., *Nucleic Acids Res.* 22:5456-5465 (1994). Immobilization can be accomplished either by in situ DNA synthesis (Maskos and Southern, supra) or by covalent attachment of chemically synthesized oligonucleotides (Guo et al., supra) in combination with robotic arraying technologies.

(iv) In addition to the solid-phase technology represented by microarray arrays, gene expression can also be quantified using liquid-phase assays. One such system is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers form specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR (r) Green 1, is an example of an intercalating dye, that preferentially binds to dsDNA resulting in a concomitant increase in the fluorescent signal. Sequence specific probes, such as used with TaqMan technology, consist of a fluorochrome and a quenching molecule covalently bound to opposite ends of an oligonucleotide. The probe is designed to selectively bind the target DNA sequence between the two primers. When the DNA strands are synthesized during the PCR reaction, the fluorochrome is cleaved from the probe by the exonuclease activity of the polymerase resulting in signal dequenching. The probe signalling method can be more specific than the intercalating dye method, but in each case, signal strength is proportional to the dsDNA product produced. Each type of quantification method can be used in multi-well liquid phase arrays with each well representing primers and/or probes specific to nucleic acid sequences of interest. When used with messenger RNA preparations of tissues or cell lines, an array of probe/primer reactions can simultaneously quantify the expression of multiple gene products of interest. See Germer et al., *Genome Res.* 10:258-266 (2000); Heid et al., *Genome Res.* 6:986-994 (1996).

(v) Measurement of altered IRF9 protein levels in cell extracts, for example by immunoassay.

Testing for proteinaceous neoplastic marker expression product in a biological sample can be performed by any one of a number of suitable methods which are well known to those skilled in the art. Examples of suitable methods include, but are not limited to, antibody screening of tissue sections, biopsy specimens or bodily fluid samples.

To the extent that antibody based methods of diagnosis are used, the presence of the marker protein may be determined in a number of ways such as by Western blotting, ELISA or flow cytometry procedures. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample. Variations on the forward assay include a simultaneous assay, in which both sample and labelled antibody are added simultaneously to the bound antibody. These techniques are well known to those skilled in the art, including any minor variations as will be readily apparent.

In the typical forward sandwich assay, a first antibody having specificity for the marker or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking, covalently binding or physically adsorbing, the polymer-antibody complex is washed in preparation for the test sample. An aliquot of the sample to be tested is then added to the solid phase complex and incubated for a period of time sufficient (e.g. 2-40 minutes) and under suitable conditions (e.g. 25° C.) to allow binding of any subunit present in the antibody. Following the incubation period, the antibody subunit solid phase is washed and dried and incubated with a second antibody specific for a portion of the antigen. The second antibody is linked to a reporter molecule which is used to indicate the binding of the second antibody to the antigen.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. "Reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed.

(vi) To the extent that one elects to screen for the phosphorylation status of these proteins, this can be achieved either qualitatively or quantitatively. At its simplest, assessment by eye of the intensity of a band which has developed, such as on an autoradiograph following incorporation of a radioactive phosphate (e.g. [$^{32}$P]-γATP) or immunoblotting using an antibody that specifically recognises the phosphorylated residue, in isolation (i.e. the presence/absence of any phosphorylation) or relative to a control test may be performed, wherein a darker and/or thicker band is indicative of a higher level of phosphorylation than a fainter and/or thinner band. A corresponding type of analysis can be qualitatively or quantitatively performed with reporter readouts. More sophisticated analysis can be performed utilising equipment such as a densitometer based on visible light or fluorescence, which can empirically calculate the concentration of a phosphorylated protein in a given band relative to a standard.

In a related aspect, the present findings have enabled the development of means for treating triple-negative breast neoplasms, in particular those which are characterised by an increased risk of metastatic spread and/or a poor survival prognosis and/or which are resistant to conventional therapeutic treatment regimes. In relation to this latter class of tumours, it has been still further determined that these tumours can be re-sensitised and thereby rendered responsive to a neoplastic treatment regime which is based on the use of the combination of agents hereinafter described. These treatments may be used on their own or as an adjunct therapy to whatever other treatment regime may have been selected to target the neoplasia. For example, it may be that the primary tumour is surgically removed and the subject treatment method is subsequently applied in order to prophylactically or therapeutically treat metastatic spread. In another example, the primary tumour may not be surgically removable and is being treated by radiation therapy while nevertheless simultaneously treating the patient for metastatic spread using the administration of IFN alone. Alternatively, the methods described herein may be used on their own.

Without limiting the present invention in any way, it would be appreciated that the diagnostic method herein disclosed identifies the risk of metastatic spread and poor survival outcome. In some cases metastatic spread may already have commenced while in other clinical situations, although a poor outcome is prognosed and metastatic spread deemed likely, the actual spread of neoplastic cells to other organs may not yet have occurred. It is to be expected that other than in the more advanced stages of metastatic cancer, where the metastatic tumours become more highly visible, one may not be able to confirm whether or not metastatic spread of the primary tumour has occurred. Accordingly, the method of the present invention may be functioning prophylactically, such as where a primary tumour exhibiting a poor prognostic outcome cannot be surgically removed but has not yet actually spread, or it may be functioning therapeutically, such as where metastatic spread has commenced, even if these metastases are not yet detectable by conventional diagnostic techniques.

Although the treatment method of this aspect of the present invention has utility in the treatment of either advanced stage or early stage disease, its application in preventing or treating early stage disease is particularly significant since this provides a means of potentially preventing a patient from reaching the point of advanced disease, which can be both debilitating and lead to mortality due to the range of other clinical problems which are associated with advanced stage disease and which can render late stage treatments less effective. To date, however, there has not been an effective means of classifying triple-negative cancers in terms of their therapeutic responsiveness and thereafter treating these cancers, even at an early stage. Accordingly, the method of the invention is very significant. Chemotherapy is the primary treatment used to date, this being very non-specific and of only moderate effectiveness with respect to this particularly aggressive and difficult to treat breast cancer subtype. Clinicians have also been reluctant to subject patients to this treatment regime, due to its side effects, where there has been no clinical indication of metastatic disease. Often it is the case that by the time metastases are diagnosable, though, they are relatively advanced and treatment is futile. The fact that the method of the present invention has now, for the first time, provided a means to accurately and simply determine the likely prognosis of a patient suffering from this form of breast cancer, the means to identify which cancers are likely to be responsive to certain treatment regimes and to treat these cancers is a significant step forward in the field of oncology. Even where it is sought to use a treatment regime such as chemotherapy, it can at least now be targeted to cancers which are likely to favourably respond. It should be understood that even where a good prognosis is obtained, it may be desirable to nevertheless treat the patient in an effort to achieve cure. Significantly, however, the present invention has now also enabled the rational design of neoplastic therapy since it has been determined that triple-negative breast cancers which exhibit a reduction in the expression of interferon regulatory factors such as IRF9 and PD-L1 are more likely to be resistant to conventional neoplastic therapy. However, it has also been determined that this subgroup of triple-negative cancers is capable of re-sensitisation and treatment using a combination therapy.

Accordingly, this aspect of the present invention is directed to a method of treating a triple-negative breast neoplasia in an individual, said method comprising administering an effective amount of a composition, wherein said composition comprises an agent which upregulates the level of Type I IFN in said individual.

In one embodiment, said neoplasia is characterised by a prognosis of an increased risk of metastatic spread.

In another embodiment said neoplasia is characterised by a poor survival prognosis.

Reference to a cancer with a "poor survival prognosis" or one exhibiting an "increased risk of metastatic spread" should be understood to have the same meaning as hereinbefore provided. However, as detailed above it should be understood that one may seek to treat any triple-negative breast cancer with this method, regardless of whether the patient exhibits a good prognosis or a poor prognosis, although targeting triple-negative cancers which exhibit reduced IRF9 expression has now been determined to achieve improved therapeutic responsiveness where this therapy is administered as a combination therapy. As detailed hereinbefore, this subgroup of triple-negative breast cancers are often resistant to conventional treatment regimes. The upregulation of interferon regulatory factor expression has been determined to re-sensitise these cells which, when coupled with chemotherapy or radiotherapy has enabled the effective treatment of these aggressive and hereinbefore largely untreatable tumours. Still further, it has also been determined that treating a patient with a combination of immunostimulation (in particular activation of $T_c$ and/or NK cells) together with anti-PD1 is also effective.

In a related aspect there is therefore provided a method of treating a triple-negative breast neoplasm, which neoplasm is characterised by a lower level of expression of IRF9 relative to the median level expressed by a corresponding neoplasm cohort, said method comprising administering an effective amount of:
(i) an immunostimulatory agent together with anti-PD1 or anti-PD-L1; or
(ii) an agent which upregulates the level of Type I IFN together with a toxin which downregulates neoplastic cell proliferation.

Reference to an "immunostimulatory agent" should be understood as a reference to any agent which activates cytotoxic T cells ($T_c$) and/or NK cells. This agent may be proteinaceous or non-proteinaceous and includes, but is not limited to polyI:C, radiotherapy, chemotherapy, IFN or other agent which upregulates IFN levels. Although chemotherapy and radiotherapy are traditionally understood to induce cell death, these treatment regimes can also effect immunostimulation.

Reference to "anti-PD1" and "anti-PDL1" should be understood as a reference to any molecule which interacts with either PD1 or PD-LI in order to prevent the interaction of the PD-L1 ligand with the PD1 receptor. In one embodiment, said molecule is an antibody.

Reference to a "toxin" should be understood as a reference to any proteinaceous or non-proteinaceous agent which acts to kill or damage a cell. The agent may be a cytotoxic agent or a non-cytotoxic agent. Without limiting the present invention to any one theory or mode of action, many such agents function via the induction of apoptotic processes. However, this is not the only mechanism by which such agents function and it is conceivable that the subject killing may be induced by some other mechanism. Examples of agents include, but are not limited to, the traditionally understood chemotherapy agents such as Actinomycin D, Arsenic Trioxide, Asparaginase, Bleomycin, Busulfan, Carboplatin, Carmustine, Chlorambucil, Cisplatin, Corticosteroids, Cyclophosphamide, Daunorubicin, Docetaxel, Doxorubicin, Epirubicin, Etoposide, Fludarabine, Fluorouracil, Gemcitabine, Hydroxyurea, Idarubicin, Ifosfamide, Irinotecan, Lomustine, Melphalan, Mercaptopurine, Methotrexate, Mitomycin, Mitoxantrone, Oxaliplatin, Paclitaxel, Procarbizine, Raltitrexed, Streptozocin, Thioguanine, Thiotepa, Topotecan, Treosulfan, Vinblastine, Vincristine, Vindesine, Vinorelbine. Other means of inducing cell damage include ionising radiation as well as the use of molecules such as inhibitors of poly-(ADP ribosyl) transferase (PARP) or agents which induce cell damage as part of a synergistic process with another agent, for example e.g. Gemcitabine or Irinotecan and CHK1/2 inhibitors such as CBP-501 or AZD7762. In addition, new classes of antineoplastic agents such as histone deacetylase inhibitors (HDACi) e.g. vorinostat, BH3 mimetics e.g. ABT737, and Tumor Necrosis Factor-Related Apoptotis-Inducing Ligand (TRAIL), are pro-apoptotic particularly when administered in conjunction with conventional cytotoxic agents. In one embodiment, said toxin is chemotherapy or radiotherapy.

Without limiting the present invention to any one theory or mode of action, human Type I IFNs bind to a specific cell surface receptor complex known as the IFN-α receptor (IFNAR) that consists of IFNAR1 and IFNAR2 chains. The mammalian Type I IFNs are designated IFN-α (alpha), IFN-β (beta), IFN-κ (kappa), IFN-δ (delta), IFN-ε (epsilon), IFN-τ (tau), IFN-ω (omega), and IFN-ζ (zeta, also known as limitin). Reference to "Type I IFN" should therefore be understood as a reference to any interferon type which falls within this class including all precursor, proprotein, or intermediate forms. It also includes reference to any isoforms which may arise from alternative splicing of Type I IFN mRNA or polymorphic forms of a Type I IFN. Reference to Type I IFN extends to any Type I IFN protein, whether existing as a dimer, multimer or fusion protein. In one embodiment, said Type I IFN is IFN-α or IFN-β.

Accordingly, in one embodiment said method of treatment comprises administering an effective amount of an agent which upregulates the level of IFN-α in said individual.

In another embodiment said method of treatment comprises administering an effective amount of a composition wherein said composition comprises an agent which upregulates the level of IFN-β in said individual.

In terms of the agent which upregulates the level of Type I IFN, this can be any suitable molecule which would be well known to the skilled person including, but not limited to:
(i) the Type I IFN protein or functional fragment thereof;
(ii) a nucleic acid molecule encoding Type I IFN or functional fragment thereof;
(iii) a proteinaceous or non-proteinaceous molecule which upregulates the expression of Type I IFN such as by modulating the transcriptional or translational regulation of the Type I IFN gene;
(iv) a proteinaceous or non-proteinaceous molecule which interacts with a Pattern Recognition receptor such as the Toll-like receptor including, for example, the TLR7/8 agonist imiquimod or the TLR3 agonists polyI:C, polyA:U; PolyI:C:L:C or the TLR9 agonist CpG.

In one embodiment, said neoplasia is characterised by a prognosis of an increased risk of metastatic spread.

In another embodiment, said neoplasia is characterised by a poor survival outcome.

In yet another embodiment said neoplasia has undergone metastatic spread.

In still yet another embodiment said method comprises administering a combination treatment selected from:
(i) poly I:C together with anti-PD1 or anti-PD-L1;
(ii) radiotherapy together with anti-PD1 or anti-PD-L1;
(iii) chemotherapy together with anti-PD1 or anti-PD-L1;

(iv) an agent which upregulates the level of Type I IFN, together with anti-PD1 or anti-PD-L1;
(v) chemotherapy together with poly I:C;
(vi) chemotherapy together with an agent which upregulates the level of Type I IFN;
(vii) radiotherapy together with poly I:C;
(viii) radiotherapy together with an agent which upregulates the level of Type I IFN.

In still another embodiment, said chemotherapy is doxorubicin.

In yet another embodiment, said agent which upregulates the level of Type I IFN is a Type I IFN.

In yet still another embodiment, said anti-PD1 or anti-PD-L1 is an antibody directed to PD1 or PD-L1, more particularly an anti-PD1 antibody.

An "effective amount" means an amount necessary at least partly to attain the desired response, or to prevent or to delay the onset or inhibit progression or halt altogether, the onset or progression of a particular condition being treated. This amount varies depending upon the health and physical condition of the individual to be treated, the taxonomic group of the individual to be treated, the capacity of the individual's immune system to stimulate a specific immune response, the degree of protection desired, the formulation of the vaccine, the assessment of the medical situation, and other relevant factors. It is expected that the amount will fall in a relatively broad range that can be determined through routine trials.

In a related aspect there is provided the use of an agent which upregulates the level of Type I IFN in the manufacture of a medicament for the treatment of a triple-negative breast neoplasm in an individual.

In another embodiment there is provided the use of:
(i) an immunostimulatory agent together with anti-PD1 or anti-PD-L1; or
(ii) an agent which upregulates the level of Type I IFN together with a toxin which downregulates neoplastic cell proliferation;
in the manufacture of a medicament for the treatment of a triple-negative breast neoplasm in an individual, which neoplasm is characterised by a lower level of expression of IRF9 relative to the median level expressed by a corresponding neoplasm cohort.

In one embodiment, said Type I IFN is IFN-α or IFN-β.

In another embodiment said method comprises administering a combination treatment selected from:
(i) poly I:C together with anti-PD1 or anti-PD-L1;
(ii) radiotherapy together with anti-PD1 or anti-PD-L1;
(iii) chemotherapy together with anti-PD1 or anti-PD-L1;
(iv) an agent which upregulates the level of Type I IFN, such as IFN, together with anti-PD1 or anti-PD-L1;
(v) chemotherapy together with poly I:C;
(vi) chemotherapy together with an agent which upregulates the level of Type I IFN;
(vii) radiotherapy together with poly I:C;
(viii) radiotherapy together with an agent which upregulates the level of Type I IFN.

In still another embodiment, said chemotherapy is doxorubicin.

In yet another embodiment, said agent which upregulates the level of Type I IFN is a Type I IFN.

In yet still another embodiment, said anti-PD1 or anti-PD-L1 is an antibody directed to PD1 or PD-L1, more particularly an anti-PD1 antibody.

It should be understood that to the extent that the above co-administration of two agents is performed, the reference to this co-administration means the simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order.

The proteinaceous molecules described above may be derived from any suitable source such as natural, recombinant or synthetic sources and includes fusion proteins or molecules which have been identified following, for example, natural product screening. The reference to non-proteinaceous molecules may be, for example, a reference to a nucleic acid molecule or it may be a molecule derived from natural sources, such as for example natural product screening, or may be a chemically synthesised molecule. The present invention contemplates analogues of Type I IFN expression product or small molecules capable of acting as agonists. Chemical agonists may not necessarily be derived from the Type I IFN expression product but may share certain conformational similarities. Alternatively, chemical agonists may be specifically designed to meet certain physiochemical properties.

The proteinaceous and non-proteinaceous agents which upregulate Type I IFN levels molecules referred to in points (i)-(iv), hereinbefore, are herein collectively referred to as "modulatory agents".

Screening for the modulatory agents hereinbefore defined can be achieved by any one of several suitable methods including, but in no way limited to, contacting a cell comprising the Type I IFN gene or functional equivalent or derivative thereof with an agent and screening for the modulation of Type I IFN protein production or functional activity, modulation of the expression of a nucleic acid molecule encoding Type I IFN or modulation of the activity or expression of a downstream Type I IFN cellular target. Detecting such modulation can be achieved utilising techniques such as Western blotting, electrophoretic mobility shift assays and/or the readout of reporters of Type I IFN activity such as luciferases, CAT and the like.

It should be understood that the Type I IFN gene or functional equivalent or derivative thereof may be naturally occurring in the cell which is the subject of testing or it may have been transfected into a host cell for the purpose of testing. Further, to the extent that a Type I IFN nucleic acid molecule is transfected into a cell, that molecule may comprise the entire Type I IFN gene or it may merely comprise a portion of the gene such as the portion which regulates expression of the Type I IFN product. For example, the Type I IFN promoter region may be transfected into the cell which is the subject of testing. In this regard, where only the promoter is utilised, detecting modulation of the activity of the promoter can be achieved, for example, by ligating the promoter to a reporter gene. For example, the promoter may be ligated to luciferase or a CAT reporter, the modulation of expression of which gene can be detected via modulation of fluorescence intensity or CAT reporter activity, respectively. Yet another example includes Type I IFN binding sites ligated to a minimal reporter.

These methods provide a mechanism for performing high throughput screening of putative modulatory agents such as the proteinaceous or non-proteinaceous agents comprising synthetic, combinatorial, chemical and natural libraries. These methods will also facilitate the detection of agents which bind either the Type I IFN nucleic acid molecule or expression product itself or which modulate the expression of an upstream molecule, which upstream molecule subsequently modulates Type I IFN expression or expression product activity. Accordingly, these methods provide a mechanism of detecting agents which either directly or indirectly modulate Type I IFN expression and/or activity.

The agents which are utilised in accordance with the method of the present invention may take any suitable form. For example, proteinaceous agents may be glycosylated or unglycosylated, phosphorylated or dephosphorylated to various degrees and/or may contain a range of other molecules used, linked, bound or otherwise associated with the proteins such as amino acids, lipid, carbohydrates or other peptides, polypeptides or proteins. Similarly, the subject non-proteinaceous molecules may also take any suitable form. Both the proteinaceous and non-proteinaceous agents herein described may be linked, bound otherwise associated with any other proteinaceous or non-proteinaceous molecules. For example, in one embodiment of the present invention said agent is associated with a molecule which permits its targeting to a localised region.

The subject proteinaceous or non-proteinaceous molecule may act either directly or indirectly to modulate the expression of Type I IFN or the activity of the Type I IFN expression product. Said molecule acts directly if it associates with the Type I IFN nucleic acid molecule or expression product to modulate expression or activity, respectively. Said molecule acts indirectly if it associates with a molecule other than the Type I IFN nucleic acid molecule or expression product which other molecule either directly or indirectly modulates the expression or activity of the Type I IFN nucleic acid molecule or expression product, respectively. Accordingly, the method of the present invention encompasses the regulation of Type I IFN nucleic acid molecule expression or expression product activity via the induction of a cascade of regulatory steps.

"Derivatives" of the molecules herein described include fragments, parts, portions or variants from either natural or non-natural sources. Non-natural sources include, for example, recombinant or synthetic sources. By "recombinant sources" is meant that the cellular source from which the subject molecule is harvested has been genetically altered. This may occur, for example, in order to increase or otherwise enhance the rate and volume of production by that particular cellular source. Parts or fragments include, for example, active regions of the molecule. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in a sequence has been removed and a different residue inserted in its place. Additions to amino acid sequences include fusions with other peptides, polypeptides or proteins, as detailed above.

Derivatives also include fragments having particular epitopes or parts of the entire protein fused to peptides, polypeptides or other proteinaceous or non-proteinaceous molecules. Analogues of the molecules contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues.

Derivatives of nucleic acid sequences which may be utilised in accordance with the method of the present invention may similarly be derived from single or multiple nucleotide substitutions, deletions and/or additions including fusion with other nucleic acid molecules. The derivatives of the nucleic acid molecules utilised in the present invention include oligonucleotides, PCR primers, antisense molecules, molecules suitable for use in cosuppression and fusion of nucleic acid molecules. Derivatives of nucleic acid sequences also include degenerate variants.

A "variant" or "mutant" of Type I IFN should be understood to mean molecules which exhibit at least some of the functional activity of the form of Type I IFN of which it is a variant or mutant. A variation or mutation may take any form and may be naturally or non-naturally occurring.

A "homologue" is meant that the molecule is derived from a species other than that which is being treated in accordance with the method of the present invention. This may occur, for example, where it is determined that a species other than that which is being treated produces a form of Type I IFN, for example, which exhibits similar and suitable functional characteristics to that of the Type I IFN which is naturally produced by the subject undergoing treatment.

Chemical and functional equivalents should be understood as molecules exhibiting any one or more of the functional activities of the subject molecule, which functional equivalents may be derived from any source such as being chemically synthesised or identified via screening processes such as natural product screening. For example chemical or functional equivalents can be designed and/or identified utilising well known methods such as combinatorial chemistry or high throughput screening of recombinant libraries or following natural product screening.

For example, libraries containing small organic molecules may be screened, wherein organic molecules having a large number of specific parent group substitutions are used. A general synthetic scheme may follow published methods (eg., Bunin B A, et al. (1994) *Proc. Natl. Acad. Sci. USA*, 91:4708-4712; DeWitt S H, et al. (1993) *Proc. Natl. Acad. Sci. USA*, 90:6909-6913). Briefly, at each successive synthetic step, one of a plurality of different selected substituents is added to each of a selected subset of tubes in an array, with the selection of tube subsets being such as to generate all possible permutation of the different substituents employed in producing the library. One suitable permutation strategy is outlined in U.S. Pat. No. 5,763,263.

There is currently widespread interest in using combinational libraries of random organic molecules to search for biologically active compounds (see for example U.S. Pat. No. 5,763,263). Ligands discovered by screening libraries of this type may be useful in mimicking or blocking natural ligands or interfering with the naturally occurring ligands of a biological target. In the present context, for example, they may be used as a starting point for developing Type I IFN analogues which exhibit properties such as more potent pharmacological effects. Type I IFN or a functional part thereof may according to the present invention be used in combination libraries formed by various solid-phase or solution-phase synthetic methods (see for example U.S. Pat. No. 5,763,263 and references cited therein). By use of techniques, such as that disclosed in U.S. Pat. No. 5,753,187, millions of new chemical and/or biological compounds may be routinely screened in less than a few weeks. Of the large number of compounds identified, only those exhibiting appropriate biological activity are further analysed.

With respect to high throughput library screening methods, oligomeric or small-molecule library compounds capable of interacting specifically with a selected biological agent, such as a biomolecule, a macromolecule complex, or cell, are screened utilising a combinational library device which is easily chosen by the person of skill in the art from the range of well-known methods, such as those described above. In such a method, each member of the library is screened for its ability to interact specifically with the selected agent. In practising the method, a biological agent is drawn into compound-containing tubes and allowed to interact with the individual library compound in each tube. The interaction is designed to produce a detectable signal that can be used to monitor the presence of the desired interaction. Preferably, the biological agent is present in an aqueous solution and further conditions are adapted depending on the desired interaction. Detection may be performed for example by any well-known functional or non-functional based method for the detection of substances.

Analogues of Type I IFN contemplated herein include, but are not limited to, modifications to side chains, incorporating unnatural amino acids and/or derivatives during peptide, polypeptide or protein synthesis and the use of crosslinkers and other methods which impose conformational constraints on the analogues. The specific form which such modifications can take will depend on whether the subject molecule is proteinaceous or non-proteinaceous. The nature and/or suitability of a particular modification can be routinely determined by the person of skill in the art.

Modulation of said Type I IFN functional levels may be achieved via the administration of Type I IFN, a nucleic acid molecule encoding Type I IFN or an agent which effects modulation of Type I IFN activity or Type I IFN gene expression (herein collectively referred to as "modulatory agents").

It should be understood that the term "treatment" does not necessarily imply that a subject is treated until total recovery. Accordingly, treatment includes reducing the severity of an existing condition, amelioration of the symptoms of a particular condition or preventing or otherwise reducing the risk of developing a particular condition.

Administration of a composition of the present invention in the form of a pharmaceutical composition, may be performed by any convenient means. The components of the pharmaceutical composition are contemplated to exhibit therapeutic or prophylactic activity when administered in an amount which depends on the particular case. The variation depends, for example, on the human or animal. A broad range of doses may be applicable. Dosage regimes may be adjusted to provide the optimum therapeutic response. For example, several divided doses may be administered daily, weekly, monthly or other suitable time intervals or the dose may be proportionally reduced as indicated by the exigencies of the situation.

The composition may be administered in a convenient manner such as by the oral, inhaled, intraperitoneal, subcutaneous, suppository routes or implanting (e.g. using slow release molecules). It may also be administered via non-mucosal routes, where appropriate, such as via intravenous or other such routes. The composition may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

The modulatory agents of the invention can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., the latest edition of Remington's Pharmaceutical Science, Mack Publishing Company, Easton, Pa. ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the peptide or polypeptide of the invention and on its particular physio-chemical characteristics.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed. A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

The composition of the invention, when administered orally, can be protected from digestion. This can be accomplished either by complexing the composition with a composition to render it resistant to acidic and enzymatic hydrolysis or by packaging these molecules in an appropriately resistant carrier such as a liposome. Means of protecting compounds from digestion are well known in the art, see, e.g., Fix (1996) *Pharm Res.* 13:1760-1764; Samanen (1996) *J. Pharm. Pharmacol.* 48:119-135; U.S. Pat. No. 5,391,377, describing lipid compositions for oral delivery of therapeutic agents (liposomal delivery is discussed in further detail, infra).

The composition of the invention can also be administered in sustained delivery or sustained release mechanisms, which can deliver the formulation internally. For example, biodegradable microspheres or capsules or other biodegradable polymer configurations capable of sustained delivery of a peptide can be included in the formulations of the invention (see, e.g., Putney (1998) *Nat. Biotechnol.* 16:153-157).

For inhalation, the composition of the invention can be delivered using any system known in the art, including dry powder aerosols, liquid delivery systems, air jet nebulisers, propellant systems, and the like. See, e.g., Patton (1998) *Biotechniques* 16:141-143; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the Type I IFN formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulisers.

The Type I IFN will be formulated in pharmaceutically acceptable compositions suitable for pulmonary or respiratory delivery to a patient. Particular formulations include dry powders, liquid solutions or suspensions suitable for nebulisation, and propellant formulations suitable for use in metered dose inhalers (MDI's). The preparation of such formulations is well described in the patent, scientific, and medical literatures, and the following descriptions are intended to be exemplary only.

Liquid formulations of Type I IFN for use in nebuliser systems can include components to enhance or maintain chemical stability, including chelating agents, protease inhibitors, isotonic modifiers, inert gases, and the like.

For use in metered dose inhalers, the Type I IFN of the present invention will be dissolved or suspended in a suitable aerosol propellant, such as a chlorofluorocarbon (CFC) or a hydrofluorocarbon (HFC). Suitable CFC's include trichloromonofluoromethane (propellant 11), dichlorotetrafluoroethane (propellant 114), and dichlorodifluoromethane (propellant 12). Suitable HFC's include tetrafluoroethane (HFC-134a) and heptafluoropropane (HFC-227).

Preferably, for incorporation into the aerosol propellant, the Type I IFN of the present invention will be processed into respirable particles as described below for the dry powder formulations. The particles are then suspended in the propellant, typically being coated with a surfactant to enhance their dispersion. Suitable surfactants include oleic acid, sorbitan trioleate, and various long chain diglycerides and phospholipids. Such aerosol propellant formulations may further include a lower alcohol, such as ethanol (up to 30% by weight) and other additives to maintain or enhance chemical stability and physiological acceptability.

Dry powder formulations will typically comprise the Type I IFN in a dry, usually lyophilized, form with a particular size within a preferred range for deposition within the alveolar region of the lung. Respirable powders of Type I IFN within the preferred size range can be produced by a variety of conventional techniques, such as jet-milling, spray-drying, solvent precipitation, and the like. Dry powders can then be administered to the patient in conventional dry powder inhalers (DPI's) that use the inspiratory breath through the device to disperse the powder or in air-assisted devices that use an external power source to disperse the powder into an aerosol cloud.

Dry powder devices typically require a powder mass in the range from about 1 mg to 10 mg to produce a single aerosolized dose ("puff"). Since the required dose of Type I IFN may be lower than this amount, the Type I IFN may be combined with a pharmaceutically acceptable dry bulking powder. Preferred dry bulking powders include sucrose, lactose, trehalose, human serum albumin (HSA), and glycine. Other suitable dry bulking powders include cellobiose, dextrans, maltotriose, pectin, sodium citrate, sodium ascorbate, mannitol, and the like. Typically, suitable buffers and salts may be used to stabilize the Type I IFN in solution prior to particle formation. Suitable buffers include phosphate, citrate, acetate, and tris-HCl, typically at concentrations from about 5 mM to 50 mM. Suitable salts include sodium chloride, sodium carbonate, calcium chloride, and the like. Other additives, such as chelating agents, peptidase inhibitors, and the like, which would facilitate the biological activity of the Type I IFN once it is dissolved within the lung would be appropriate. For example, ethylenediaminetetraacetic acid (EDTA) would be useful as a chelator for divalent cations which are peptidase cofactors.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's, Chapters 37-39.

The pharmaceutical compositions of the invention can be administered in a variety of unit dosage forms depending upon the method of administration. Dosages for typical modulatory pharmaceutical compositions are well known to those of skill in the art. Such dosages are typically advisorial in nature and are adjusted depending on the particular therapeutic context, patient tolerance, etc. The amount of modulatory agent adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton (1997) "Bioavailability and transport of peptides and peptide drugs into the brain" *Peptides* 18:1431-1439; Langer (1990) *Science* 249:1527-1533.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present invention is further described by reference to the following non-limiting examples.

EXAMPLE 1

Type I IFNs as Metastasis Suppressors in Breast Cancer

Measurement of primary tumour IRF9 expression in a cohort of 479 patients revealed a significant decrease in expression in the triple-negative breast cancer subtype. Only 10-15% of triple-negative breast cancer tumours retained expression of IRF9 and this was associated with a much better outcome (FIG. 1). In fact, loss of Irf9 expression was associated with an 8 times greater risk of metastasis and metastasis was rarely observed in triple-negative breast cancer patients that retained primary tumour expression of IRF9 (FIG. 1).

Figure 2:
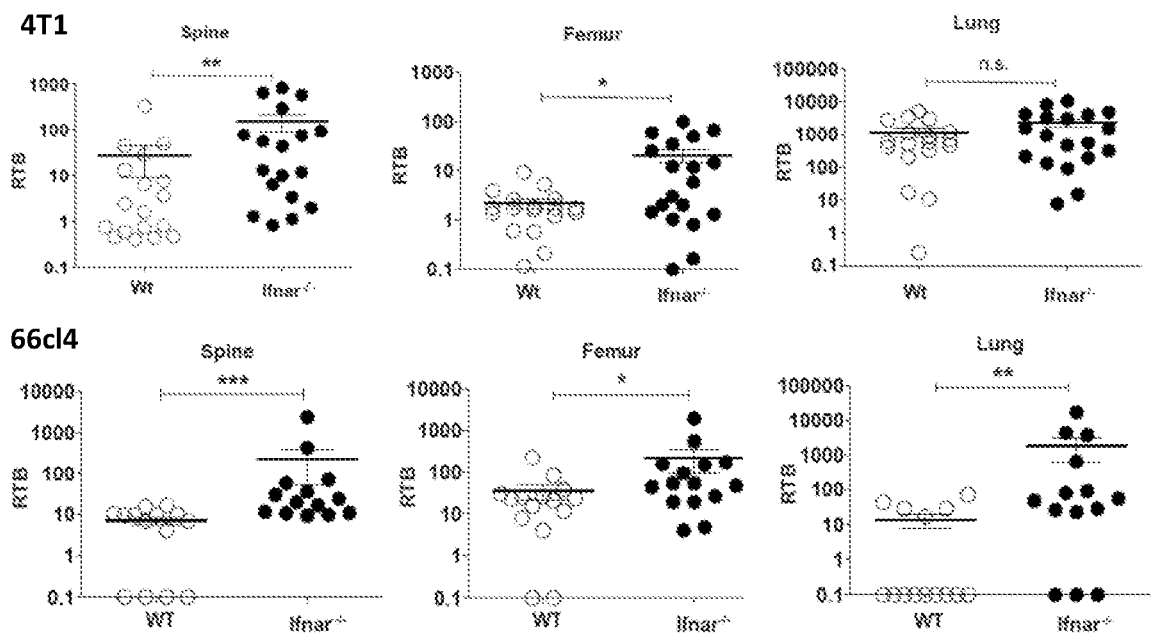
FIG. 2 is an image which depicts the loss of host IFN response increases metastasis Tumour cells (66c14 and 4T1-cherry cells) were injected into the mammary gland of balb/c mice. At end point (day 28-32), tissues were resected and tumour burden was measured by QPCR detection of cherry DNA expression (A).
Figure 3:
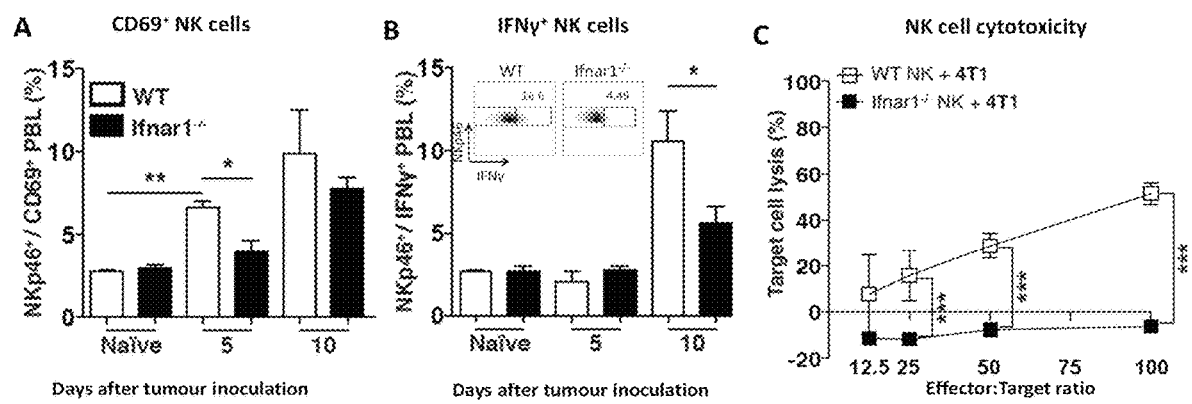
FIG. 3 is an image which depicts the loss of tumour specific NK cell activation and function in Ifnar1−/− mice WT and Ifnar1−/− balb/c mice were injected with 1×105 4T1 cells into the 4th mammary gland. On indicated days, blood samples were taken, lymphocytes isolated and stained with mAbs reactive with NKp46 and CD69 (A) or NKp46 and IFN-γ (B) and analysed by flow cytometry. C) Poly I:C activated NK cells from WT or Ifnar−/− mice were enriched and used against 4T1 cells in a calcein-AM cytotoxic assay. $*p<0.05$, results pooled from 2 independent experiments n>4.
Figure 4:
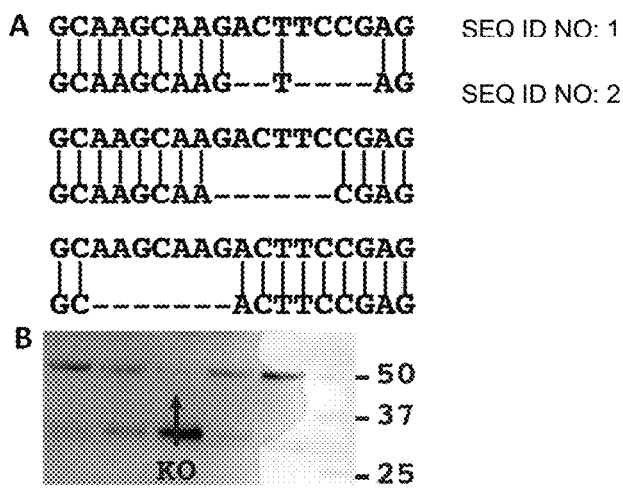
FIG. 4 is an image depicting confirmation that excision of a portion of the Irf9 DNA binding domain by sequencing (A) and Western blotting (B).

Loss of the IFN receptor Ifnar1 (using Ifnar1$^{-/-}$ mice) accelerates metastasis in the spontaneous MMTV-PyMT C57 Bl/6 model and in the 66c14 and 4T1 orthotopic BALB/c models (FIG. 2). The data suggest that type I IFN-driven metastasis suppression is driven by an anti-tumour immune response that is initiated by tumour cell intrinsic signalling. In this regard, an important requirement for type I IFN signalling in NK specific tumour cytotoxicity (FIG. 3).

Altered IFN Signalling Impacts NK Cell-Driven Tumour Cytotoxicity

Data obtained using models of triple-negative breast cancer support an important role of IFN signaling in the NK cell anti-tumour response. Mice bearing 4T1 cells have an elevated accumulation and activation of NK cells in the peripheral blood compared to naïve mice (FIG. 3A, B) suggesting an innate immune response to these tumour lines which express stress ligands such as Rael and have reduced MHC class I expression. When comparing NK cell activation in WT and Ifnar1$^{-/-}$ mice a significant decrease in the number of CD69 and IFNγ expressing NK cells was observed, suggesting that IFN signalling played an important role in tumour-specific NK cell activation and function (FIG. 3) 4T1 tumour cells are susceptible to NK cell mediated killing and cytotoxicity is reliant on intact type I IFN signaling (FIG. 3C).

EXAMPLE 2

Stratification of triple-negative breast cancer patients into good and poor prognostic groups is currently very difficult. A proportion of patients develop metastatic disease very rapidly and do not respond to the untargeted therapies currently available for this breast cancer subtype. The prognostic potential of IRF proteins in triple-negative breast cancer, including the association with immune infiltrates and stress signals, and testing the efficacy of therapies aimed at stimulating IFN-induced immunity in both early and late treatment settings are tested.

Test the Association of IRF Expression with Prognosis and Immune Infiltration and Function in Independent Cohorts of Triple-Negative Breast Cancer The initial breast cancer cohort used to generate the data in FIG. 1 comprised 53 patients with the triple-negative breast cancer subtype. This analysis is extended to an independent triple-negative breast cancer cohort of 163 patient primary tumours. The expression of IRF7 and IRF9 is measured and correlated with parameters including time to metastasis and breast cancer-specific survival. The expression of IRF proteins with TILs and also specific immune infiltrates including CD4$^+$ and CD8$^+$ T cells, NK cells and FoxP3$^+$ regulatory T cells (Tregs) is correlated and tumour cell expression of NK cell stress ligands such as MICA/B and ULBP1-6 is measured to determine correlation with IRF expression and/or prognosis.

a) Sections (formalin-fixed, paraffin embedded) of tissue microarrays (TMAs) derived from 160 triple-negative breast cancer patients with clinicopathology data and follow up information are analysed for IRF9 and IRF3/5/7 expression using immunohistochemistry (IHC), as in FIG. 1. Staining is scored for intensity and frequency. Scores are then be stratified into high, low and absent expression and groups are compared via the log rank test for time from diagnosis to metastatic relapse and breast cancer specific mortality.

b) H&E stained sections from the triple-negative breast cancer cohort (as above) are scored, including assessment of intratumoural and stromal TILs. Measurement of TILs, however, does not allow a functional assessment of the nature of the immune cell infiltrate. For this reason, IHC is used to assess CD8$^+$ T cell, CD4$^+$ T cell, NK cell and Treg infiltrates in serial TMA sections, using established antibodies and protocols (Cimino-Mathews A, Ye X, Meeker A, Argani P, Emens L A. *Metastatic triple-negative breast cancers at first relapse have fewer tumor-infiltrating lymphocytes than their matched primary breast tumors: a pilot study.* Human pathology. 2013; 44(10):2055-63). Infiltrates are compared with patient outcome and any correlations with IRF9 and 7 expression are assessed.

c) To test if tumour cell ligands of activating NK cell receptors and/or MHC class I molecules display varied expression across the triple-negative breast cancer cohort and or/correlate with IRF expression or immune infiltrates, IHC is used to measure tumour cell expression of the NKG2D ligands MICA/B, ULBP-1 and ULBP2 as described previously (de Kruijf E M, Sajet A, van Nes J G, Putter H, Smit V T, Eagle R A, et al. *NKG2D ligand tumor expression and association with clinical outcome in early breast cancer patients: an observational study.* BMC cancer. 2012; 12:24) and the DNAM1 ligand CD155.

Figure 5:
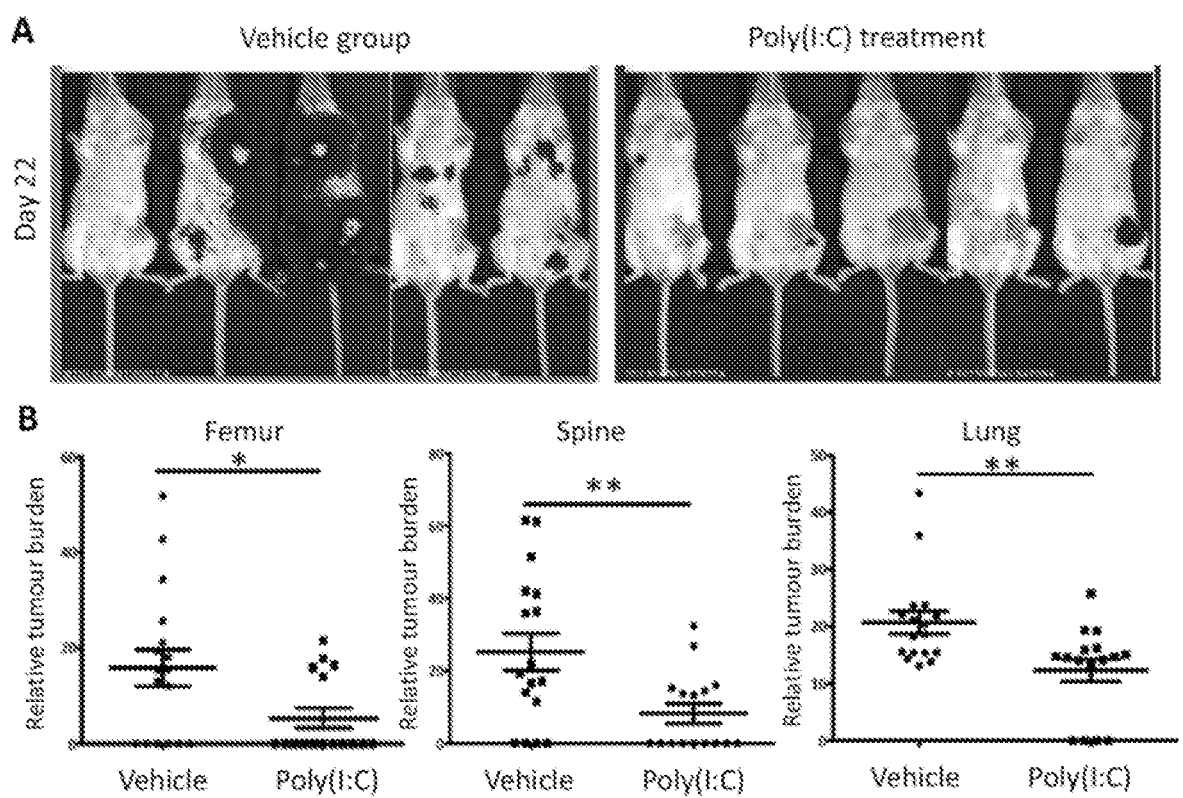
FIG. 5 is an image depicting that poly(I:C) treatment reduces metastasis to lung and bone 4T1.2-luc2 cells were injected into the mammary fat pad of balb/c mice (day 0). From day 4, mice were treated with 25 ug poly(I:C) or control 3× weekly IV. After primary tumour resection at 0.4 g, mice were monitored for metastasis by bioluminescence (A) and by QPCR analysis of luciferase expression compared to vimentin at end point (B). $*p<0.05$, $**p<0.01$.
Figure 6:
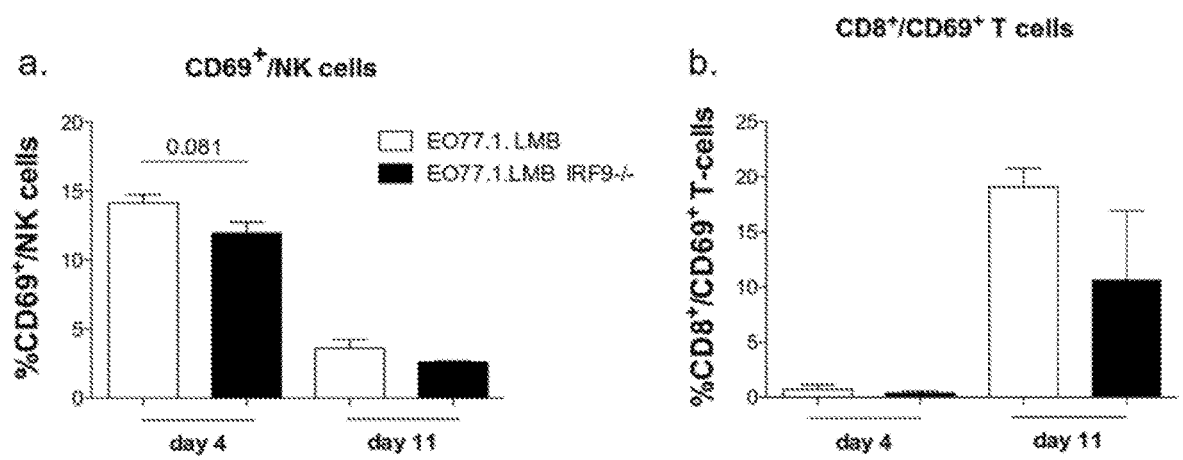
FIG. 6 is a graphical representation of the increased NK and CD8$^+$ T-cell activation by tumour cells expressing IRF9 after intracardiac injection.
Figure 7:
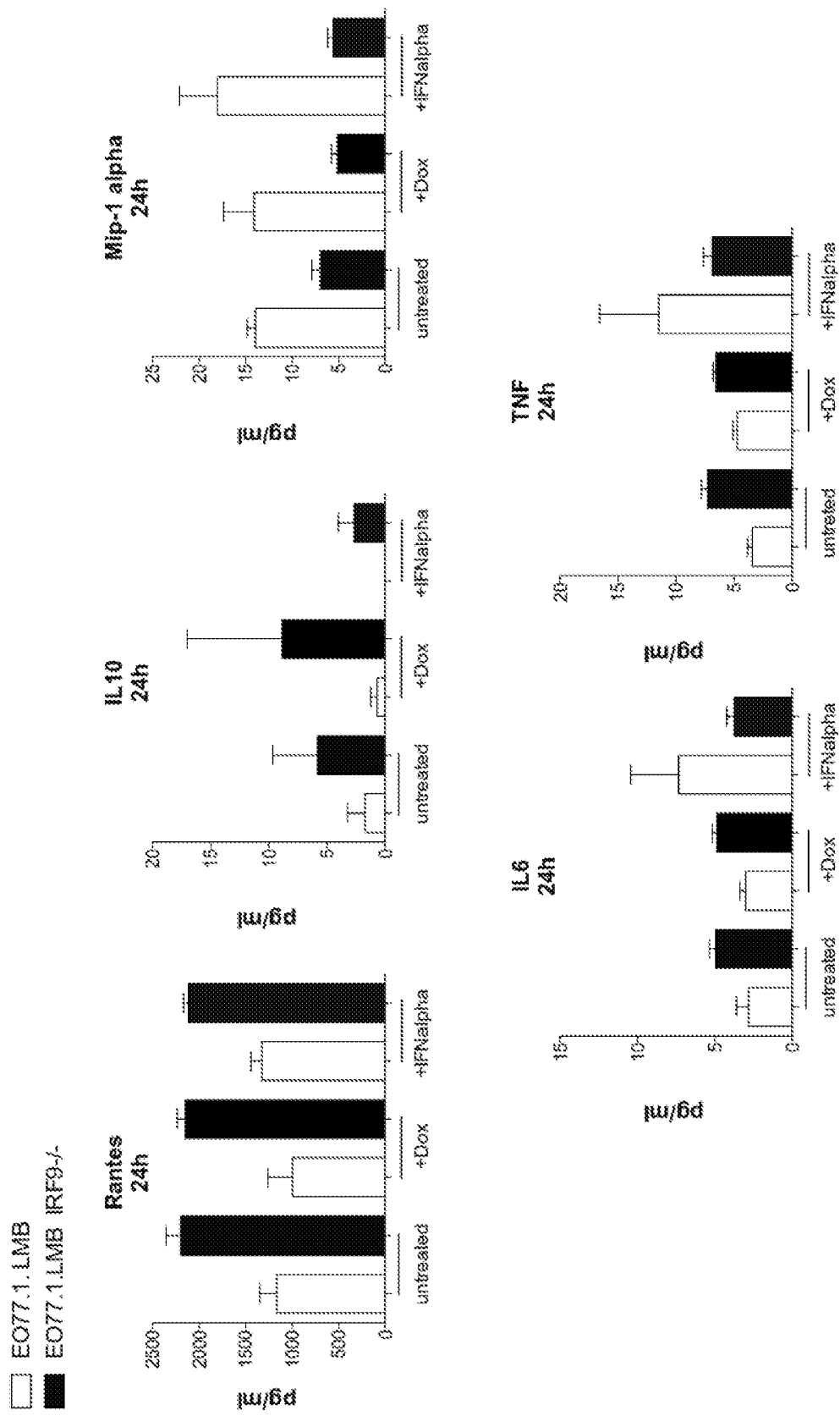
FIG. 7 is a graphical representation demonstrating the altered cytokine secretion in IRF9 knockout cancer cells that skews the immune response to a suppressed state.
Figure 8:
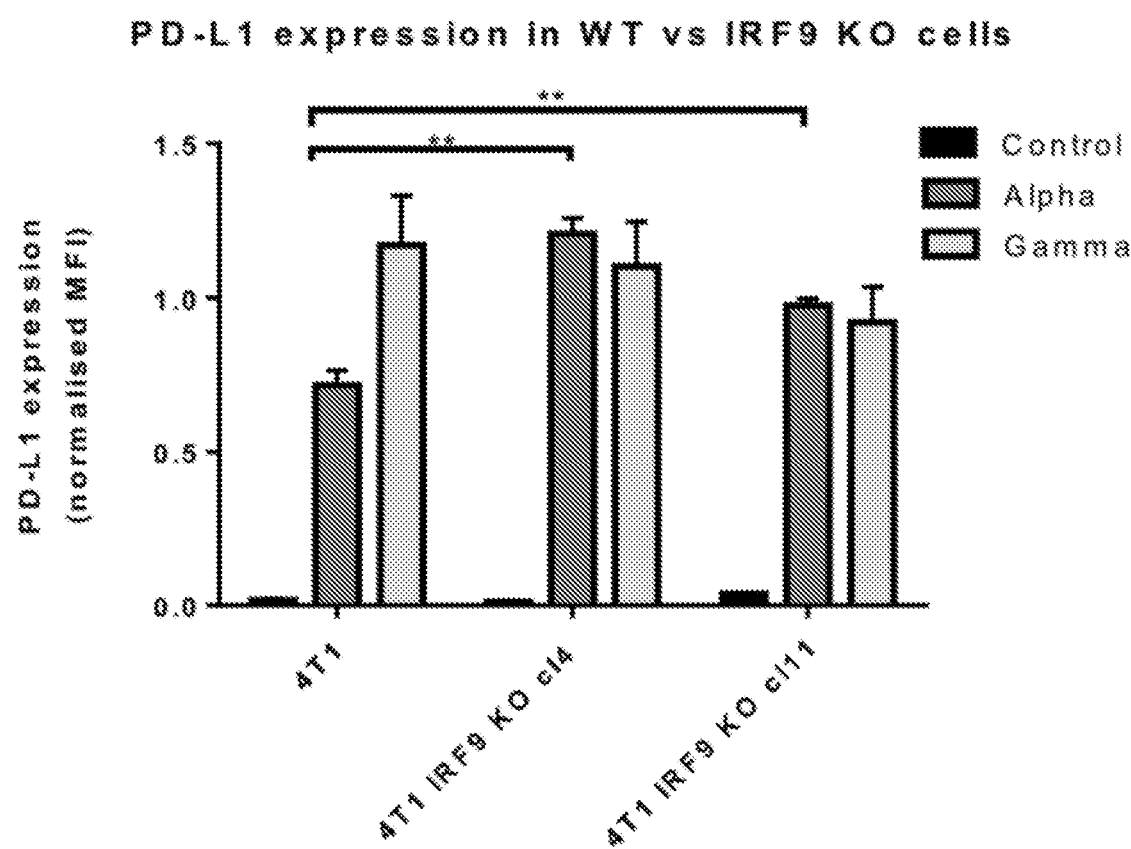
FIG. 8 is a graphical representation demonstrating that interferon treatment enhances cancer cell expression of PD-L1 and that cells lacking IRF9 induce more PD-L1. A loss of IRF9 causes PD-L1 expression to be increased after IFNα stimulation. FACS analysis for PD-L1 cell surface expression using PE tagged anti-PD-L1, MIH5 (1:50). Cells were treated with IFNα (1000 IU/ml) or IFNγ (10 ng/ml) for 48 hours prior to FACS. Data is represented as normalised mean fluorescence intensity (MFI). Error bars represent SEM, n=3. Statistical significance values equal: $**p<0.01$.
Figure 9:
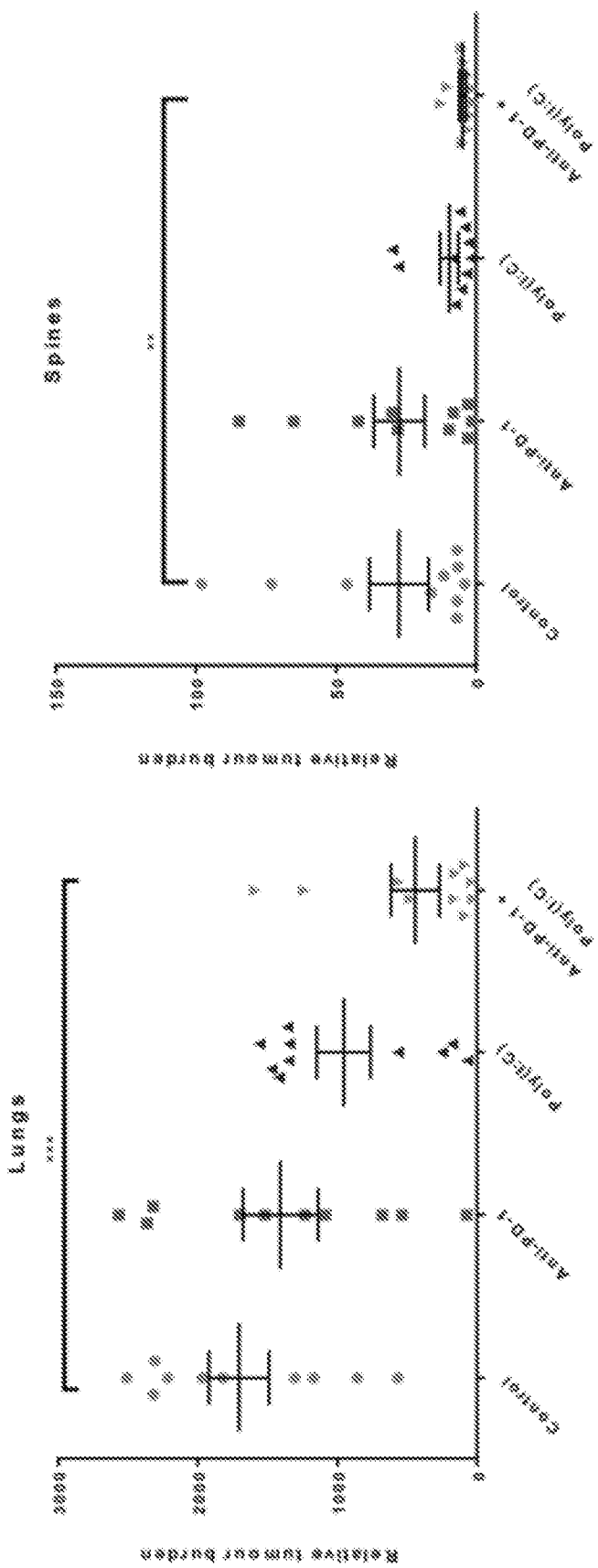
FIG. 9 is a graphical representation which demonstrates that the combination of poly I:C and anti-PD1 effectively reduces metastasis and prolongs survival in the aggressive E0771. 4T1.2 tumour burden in lungs and spines of Balb/c mice is reduced after treatment with anti-PD-1 and poly (I:C). Relative tumour burden (RTB) in the lung was determined by qRT-PCR based on the amplification cycle at which a change in basal fluorescence was detected. Scores were calculated using mean regression quantification cycle (Cq) values according to the formula described by Eckhardt et al. (2005). Disseminated tumour cells were identified by mCherry, while mVimentin was used as a loading control. Error bars represent SEM, n=10. Statistical significance values:
$*p=0.0005$, $p=0.0052$.
Figure 10:
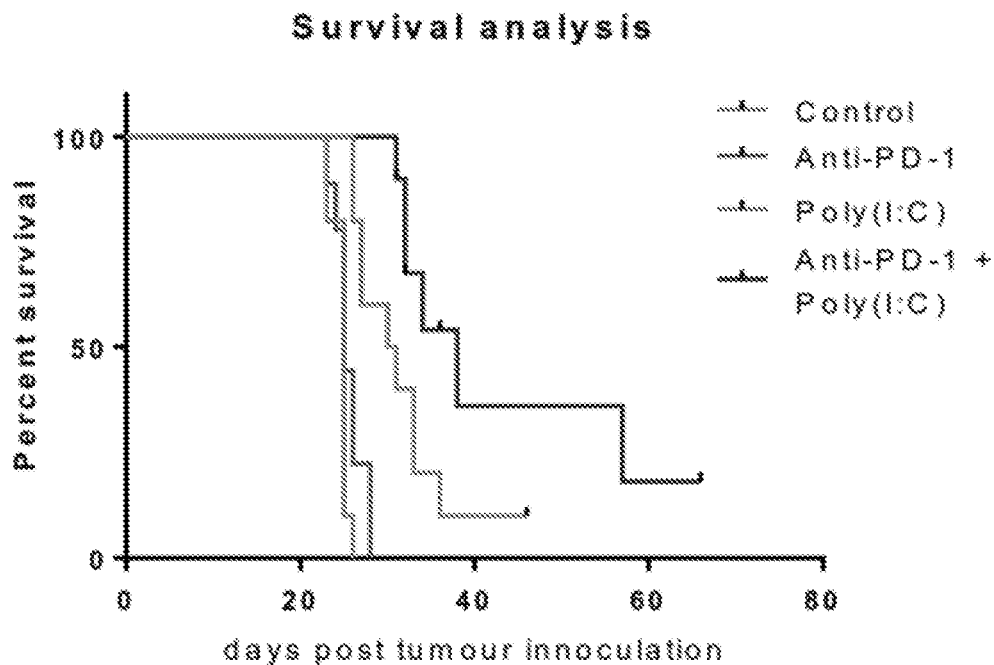
FIG. 10 is a graphical representation of combination therapy involving anti-PD-1 and poly (I:C) significantly increases survival time. Groups of 10 balb/c mice were injected with 5×104 4T1.2 cells IMFP. Mice received 5× poly (I:C) and 4× anti-PD-1 from days 2-12. Primary tumour resection occurred on day 12. Mice were culled at signs of metastasis, survival time is represented as days post tumour inoculation. $P<0.001$
Figure 11:
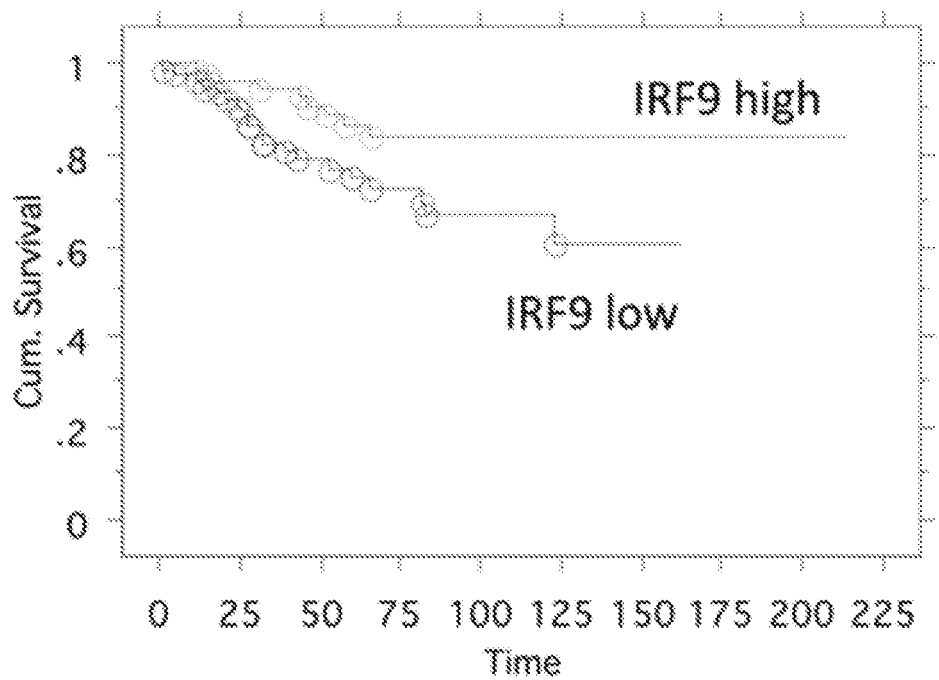
FIG. 11 is a graphical representation depicting that IRF9 is a good prognostic factor in another independent cohort of patients with triple-negative breast cancer, Kaplan-Meier Cum. Survival plot for FU to Death, Censor Variable: BrCa Death Score; Grouping Variable: av IRF %>median 13%; RPA cohort: 147 patients with TNBC.
Figure 12:
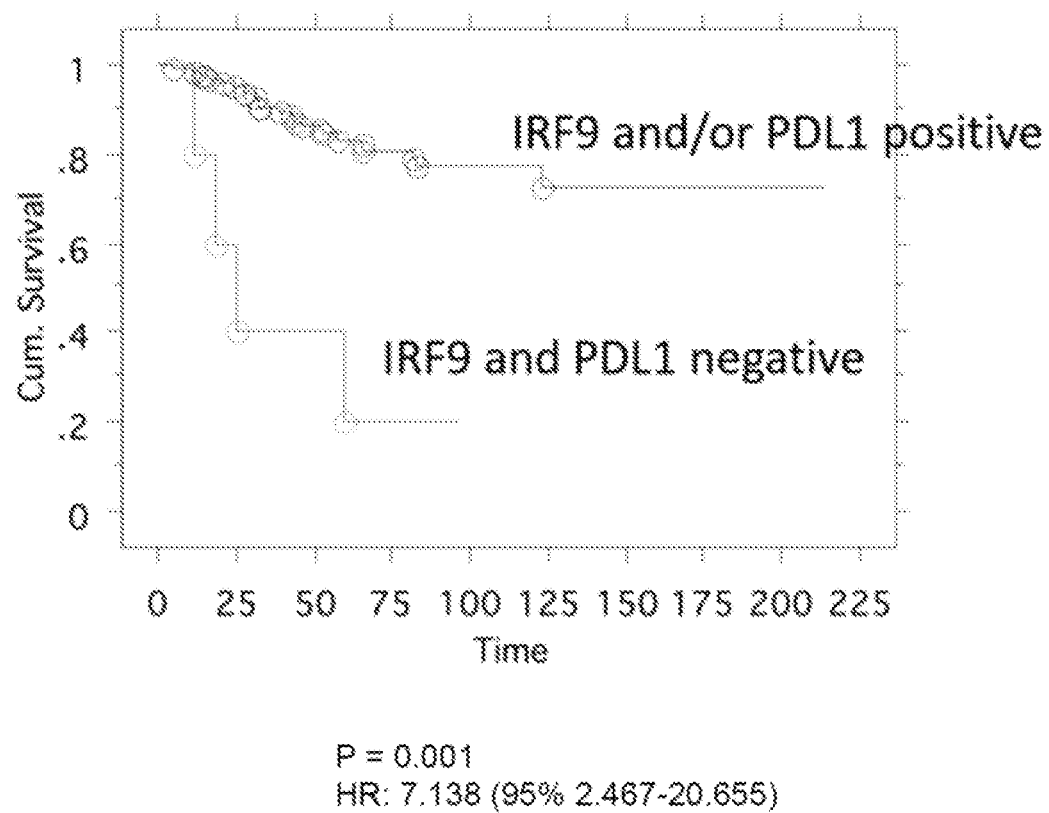
FIG. 12 is a graphical representation depicting that the loss of IRF9 and PD-L1 predicts much worse outcome in TNBC patients; Kaplan-Meier Cum. survival plot for BrCa Death FU; censor variable: BrCa Death Score; grouping variable: PD-L1 stroma neg and IRFP9 negative. RPA cohort: 147 patients with TNBC.
Figure 13:
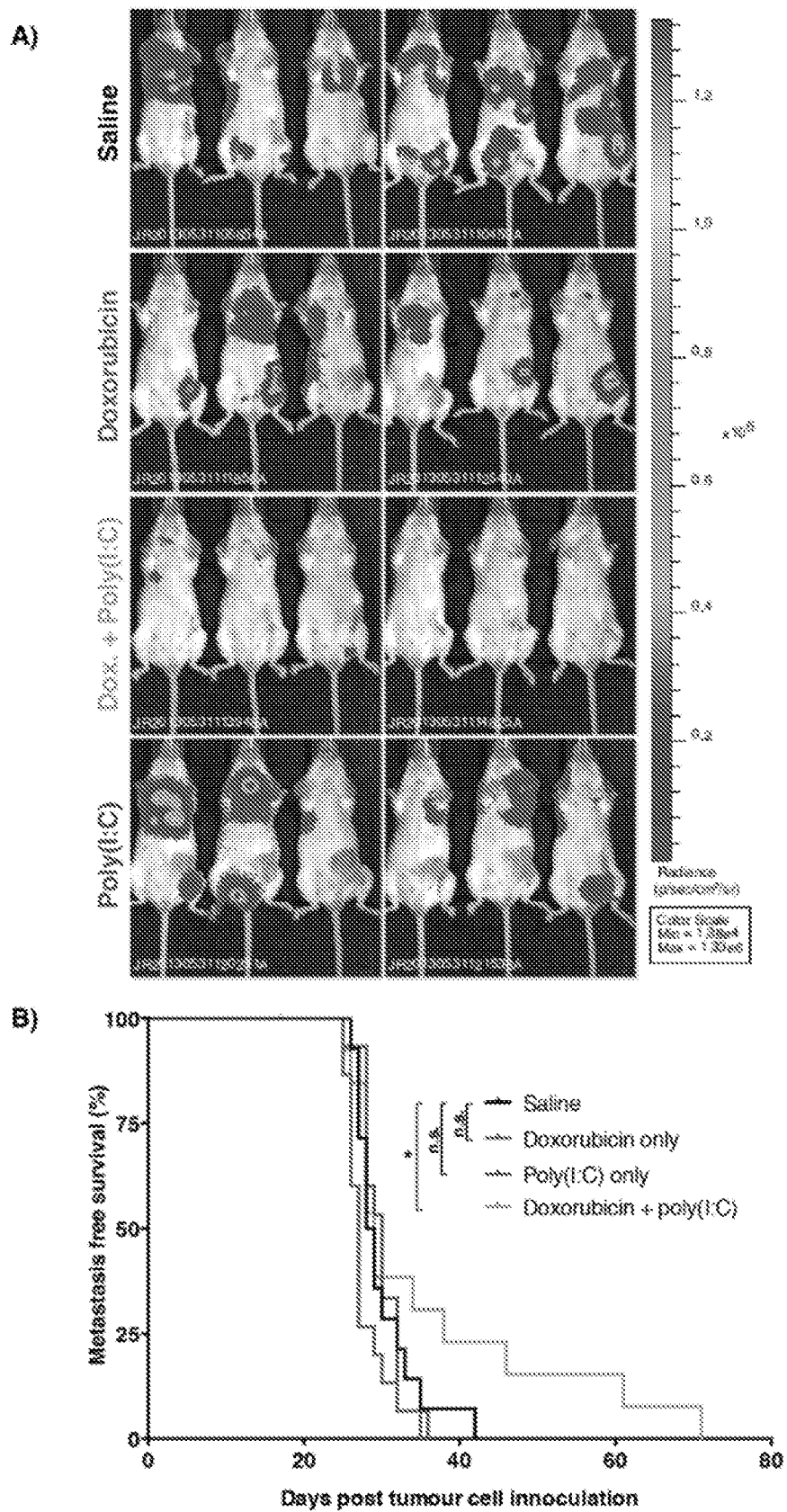
FIG. 13 is an image depicting that combination Poly(I:C) and doxorubicin therapy extends survival in the late metastatic treatment setting. Female Balb/c mice had primary tumours surgically removed 12 days after cell inoculation (100,000 4T1.2-Luc2 IMFP). As indicated, poly(I:C) (25 µg, I.V., thrice weekly) and/or doxorubicin (4 mg/kg, I.V., twice weekly) therapy began on D14 post tumour cell injection with weekly bioluminescent imaging. (A) Is a representative image of all groups 23 days post tumour cell inoculation and (B) mice were individually culled at first signs of metastatic distress in order to examine the impact of therapy on survival. n=15 mice per group, $*p<0.05$ using a Mantel-Cox test.
Figure 14:
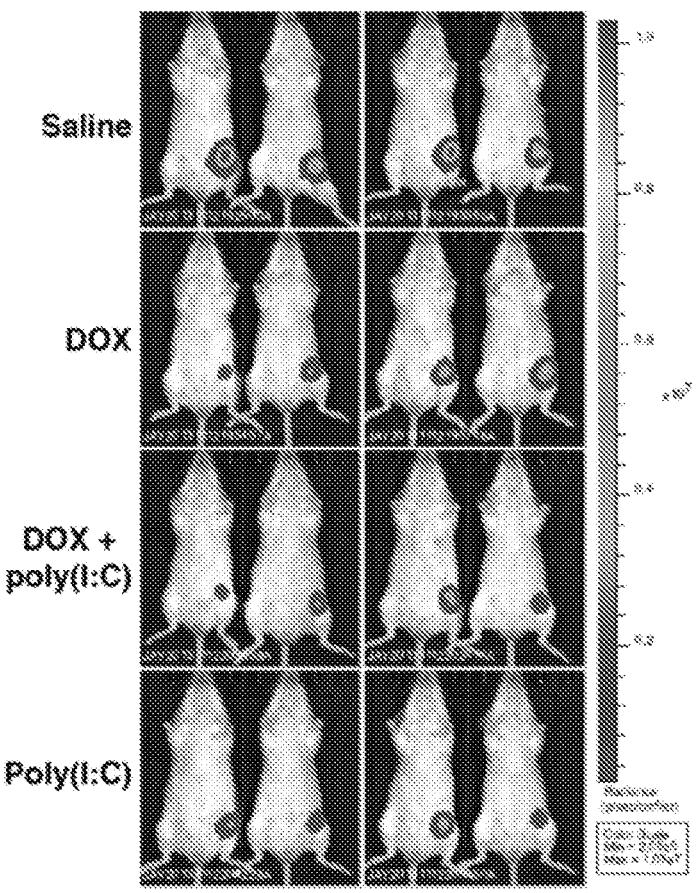
FIG. 14 is an image depicting that neo-adjuvant poly(I:C) therapy reduces primary tumour growth. Female 8-week-old Balb/c mice were administered poly(I:C) (25 µg, I.V., thrice weekly) and/or doxorubicin (4 mg/kg, twice weekly) beginning 2 days post tumour cell inoculation (100,000 4T1.2-Luc2 IMFP). Differences in primary tumour growth were detectable 6 days after tumour cell inoculation using bioluminescent imaging (of four mice representative of the larger cohort) (A). Therapy was ceased and primary tumours were surgically removed and weighed 12 days post tumour cell injection (B). n=10 mice per group, error bars represent the 95% CI, $*p<0.05$, $p<0.01$, $*p<0.001$ using Student's t-tests.
Figure 14:
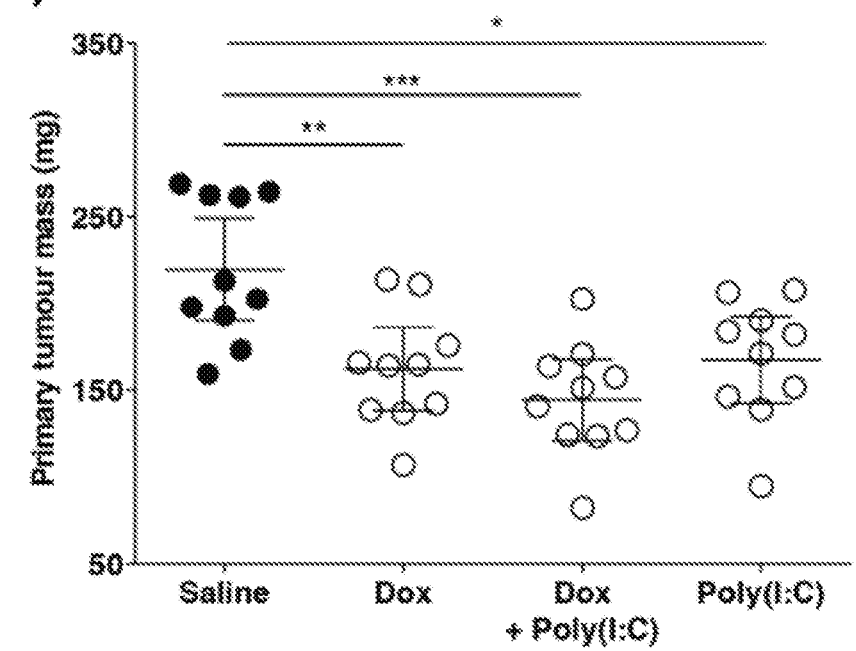
Figure 15:
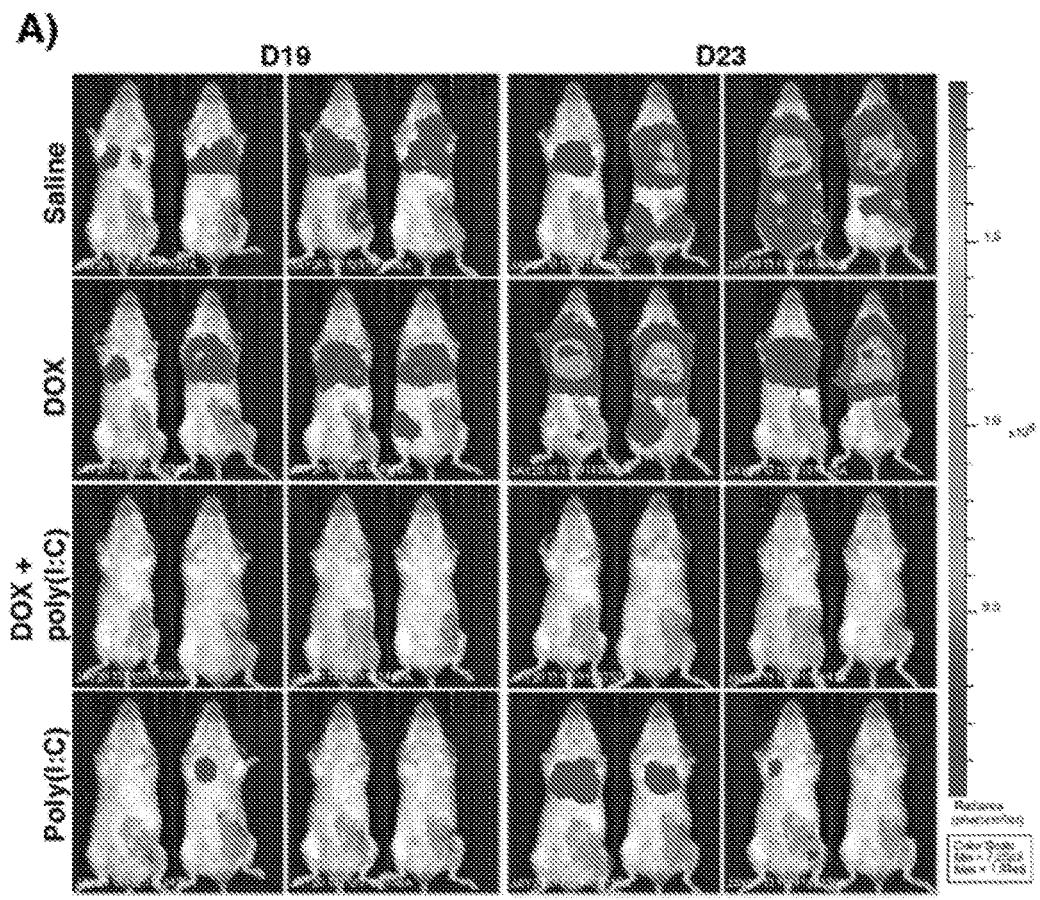
FIG. 15 is an image depicting that neo-adjuvant poly(I:C) therapy prolongs survival. Mice used in FIG. 2 continued to undergo weekly bioluminescent imaging to visualise the kinetics of metastatic spread. (A) Images taken 19 and 23 days post tumour cell inoculation are of the same four mice in identical order and representative of the larger cohort. (B) Mice were individually sacrificed at first signs of metastatic distress and dates recorded to generate Kaplan-Meier survival estimates. Differences in survival between groups were tested for significance using a Mantel-Cox test. n=10 mice per group, ***p<0.001.
Figure 15:
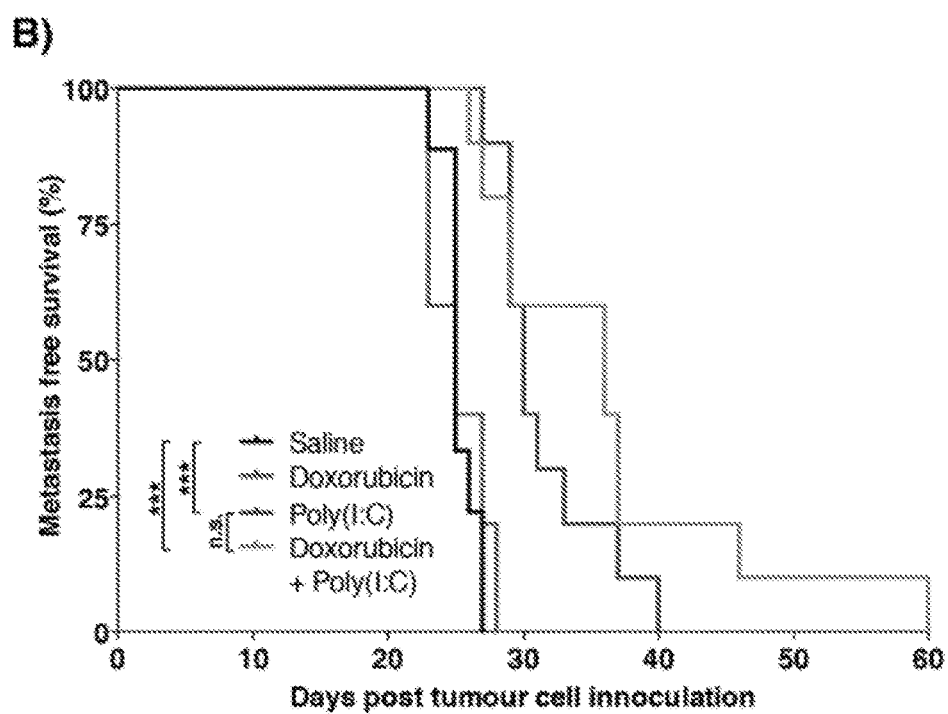

Test the Consequences of Irf9 Knockout in Triple-Negative Breast Cancer Cell Lines and Syngeneic Models Expression of Irf9 is knocked out in balb/c (66c14, 4T1) and C57 Bl/6 (EO771, PyMT) mouse cell lines and the impact on tumour cell proliferation and orthotopic tumour growth and metastasis in vivo, is required. Associated changes in tumour infiltating and circulating immune cells, impact on tumour cell susceptibility to immune effector cells in vitro and the impact of NK cell specific loss of IFN signalling is measured.
a) Using TALEN technology (Boch J. *TALEs of genome targeting.* Nature biotechnology. 2011; 29(2):135-6) an Irf9 knockout 4T1 cell line has been generated (FIG. 5). This is repeated in 66c14, EO771 and PyMT cell lines. Given that Irf7 is induced by the ISGF3 complex of STAT1/2 and Irf9, Irf9 loss will likely directly result in reduction of Irf7. Irf7 we can also be knocked out directly in these cells.

The impact of Irf9 loss is measured on cellular proliferation using the SRB assay. To measure the impact of Irf9 on metastasis, tumour cells with intact or knockout Irf9 expression (1000-1×10$^5$ cells) are injected into the 4$^{th}$ mammary gland of 6-8 week old female Balb/c or C57 B1/6 mice (20 mice/group). Primary tumour monitoring and quantitation of metastatic burden in organs such as lung, spine and femur is performed as previously described (Bidwell B N, Slaney C Y, Withana N P, Forster S, Cao Y, Loi S, et al. *Silencing of Irf7 pathways in breast cancer cells promotes bone metastasis through immune escape.* Nature medicine. 2012; 18(8):1224-31; Cao Y, Slaney C Y, Bidwell B N, Parker B S, Johnstone C N, Rautela J, et al. *BMP4 inhibits breast cancer metastasis by blocking myeloid-derived suppressor cell activity.* Cancer research. 2014; 74(18): 5091-102; 32 Withana N P, Blum G, Sameni M, Slaney C, Anbalagan A, Olive M B, et al. *Cathepsin B inhibition limits bone metastasis in breast cancer.* Cancer research. 2012; 72(5):1199-209; Eckhardt B L, Parker B S, van Laar R K, Restall C M, Natoli A L, Tavaria M D, et al. *Genomic analysis of a spontaneous model of breast cancer metastasis to bone reveals a role for the extracellular matrix.* Molecular cancer research: MCR. 2005; 3(1):1-13) by bioluminescent imaging followed by histology (5 mice/group) or real time qPCR (ABI PRISM 7000) and Taqman chemistry (15 mice/group), comparing the ratio of genomic levels of cherry or luciferase in the tumour cells to the vimentin gene present in all cells of that organ (Eckhardt B L, Parker B S, van Laar R K, Restall C M, Natoli A L, Tavaria M D, et al. *Genomic analysis of a spontaneous model of breast cancer metastasis to bone reveals a role for the extracellular matrix.* Molecular cancer research: MCR. 2005; 3(1):1-13). Differences in primary tumour growth and metastatic burden between the groups at set time points is tested using an unpaired Student's t-test (where data are normally distributed) or by the Mann-Whitney rank sum test (Sigma-Stat). For metastasis-free survival studies, primary tumours are resected when they reach 0.3-0.4 g and mice are terminally anesthetized when signs of metastasis are evident. For univariate analysis, Kaplan-Meier curves are generated and compared with the log rank test.
b) Measurement of immune cell subsets is performed using multi-colour flow cytometry. At designated time points, the peripheral blood, primary tumours and organs including lung and bone marrow are harvested and processed into a single cell suspension followed by ammonium chloride red blood cell lysis followed by staining with a panel of antibodies to detect NK cells (NKp46$^+$TCRβ$^-$), CD8$^+$ T cells (CD8$^+$TCRβ$^+$), CD4$^+$ T cells and regulatory T cells (CD4$^+$TCRβ$^+$ Foxp3$^{+/-}$ CD25$^{+/-}$), and MDSC (CD11b$^+$Gr1$^+$Ly6G$^{+/-}$Ly6C$^{+/-}$). The activation and function of NK cells is measured by measuring the expression of NKG2D, DNAM-1 and IFNγ on NKp46$^+$ NK cells. For the analysis of changes to NK cell ligands (CD155, MULT1, Rae-1, H60) or MHC class I molecules (H2D(d), H2K(d)) present on the tumour cell surface, a panel of antibodies is used (Andrews D M, Sullivan L C, Baschuk N, Chan C J, Berry R, Cotterell C L, et al. *Recognition of the nonclassical MHC class I molecule H2-M3 by the receptor Ly49A regulates the licensing and activation of NK cells.* Nature immunology. 2012; 13(12):1171-7; Chan C J, Martinet L, Gilfillan S, Souza-Fonseca-Guimaraes F, Chow M T, Town L, et al. *The receptors CD96 and CD226 oppose each other in the regulation of natural killer cell functions.* Nature immunology. 2014; 15(5): 431-8). This allows identification of alterations in immune activation and suppression with loss of tumour intrinsic Irf9.
c) To test the impact of Irf9 loss on NK cell function, cytotoxicity assays as described elsewhere are used (Neri S, Mariani E, Meneghetti A, Cattini L, Facchini A. *Calcein-acetyoxymethyl cytotoxicity assay: standardization of a method allowing additional analyses on recovered effector cells and supernatants.* Clin Diagn Lab Immunol. 2001; 8(6):1131-5), as performed in FIG. 3. Briefly, splenic NK cells from naïve or Poly(I:C) activated (250 μg for 48 hrs) WT or Ifnar$^{-/-}$ animals are immune-magnetically enriched. Target tumour cells are calcein labelled prior to incubation with NK cells (or alone) at varied ratios for >4 h prior to fluorescent quantitation of calcein release.

To test if NK cells are a direct target of tumour IFN-induced metastasis suppression the experiments outlined in a) are carried out in mice deficient in Ifnar1 selectively in the NK cell compartment (NKp46-Cre-Ifnar1).

Measure the Impact and Targets of Type I IFN Based Therapeutics in Models of Triple-Negative Breast Cancer Tumour-bearing mice are treated with poly(I:C), a stable derivative of poly(I:C):poly ICLC that is currently in clinical trials (Hiltonol™, Oncovir) or recombinant IFNα$_1$ in early and late treatment settings and the impact of such treatments on immune activation and function, primary tumour growth and metastasis is measured. Treatment is then combined with chemotherapy, commonly used to treat triple-negative breast cancer patients to assess the additive therapeutic benefit. Mice bearing BALB/c (4T1, 4T1.2) and C57 B1/6 (EO771) syngeneic tumours are treated with poly(I:C) or IFNα1 using two approaches 1) administration when primary tumours just palpable (~day 3-5) and cessation of treatment on the day of primary tumour resection, before detection of metastases 2) excision of the primary tumour (when 0.4 g) and initiation of treatment when metastatic burden is evident by bioluminescence.

a) The current therapeutic options for patients with triple-negative breast cancer are chemotherapeutics such as the topisomerase II poison doxorubicin. Not only is chemotherapy not effective in some patients with triple-negative breast cancer, treatment with agents such as doxorubicin has previously been associated with increased tumour cell immunogenicity. The combined impact of poly(I:C) and doxorubicin chemotherapy is therefore tested. Tumour-bearing mice are treated with poly(I:C) as above as a single agent or in combination with 4 mg/kg doxorubicin twice weekly via intravenous injection.

b) Immune cell accumulation, activation and function is measured after therapy to determine if metastasis suppression is associated with an anti-tumour immune response. This includes measurement of tumour infiltrating and circulating immune effector and suppressor cells and alterations to the tumour cells themselves, including changes to the MHC class I molecules and NKG2D ligands.

Evaluate Predictive Markers of Response to IFN-Based Therapeutics

Poly(I:C) therapy is tested in terms of whether it reduces metastasis in mice bearing tumours deficient in IRF9, if tumours that have lost Irf9 retain expression of NK cell stress ligands, and if measurement of an active IFN pathway systemically has potential to predict therapeutic response.

a) Irf9 knockout and control 4T1 cell lines are treated with poly(I:C). The impact on metastasis is tested using methods above.

b) Irf9 knockout cells are tested as to whether they retain cell surface expression of the NKG2D ligands Rae 1, MULTI and H60 and the balance of these activating ligands is compared to NK cell inibitory MHC class I (H2D(d) and H2K(d)) proteins. Cell lines are assessed for expression of these cell surface proteins by flow cytometry.

c) To directly measure systemic IFN activation, phosphorylated STAT1 in blood samples is measured from both mouse models with altered Irf9 expression or those treated with poly(I:C) using phospho-flow cytometry and the anti-mouse/human pSTAT1 antibody (pY701).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Abramson V G, Lehmann B D, Ballinger T J, Pietenpol J A. *Subtyping of triple-negative breast cancer: implications for therapy*. Cancer. 2015; 121(1):8-16

Andrews D M, Sullivan L C, Baschuk N, Chan C J, Berry R, Cotterell C L, et al. *Recognition of the nonclassical MHC class I molecule H2-M3 by the receptor Ly49A regulates the licensing and activation of NK cells*. Nature immunology. 2012; 13(12):1171-7

Alon et al., *Proc. Natl. Acad. Sci. USA:* 96,6745-76750, June 1999

Bidwell B N, Slaney C Y, Withana N P, Forster S, Cao Y, Loi S, et al. *Silencing of Irf7 pathways in breast cancer cells promotes bone metastasis through immune escape*. Nature medicine. 2012; 18(8):1224-31

Boch J. *TALEs of genome targeting*. Nature biotechnology. 2011; 29(2):135-6

Bunin B A, et al. (1994) *Proc. Natl. Acad. Sci. USA,* 91:4708-4712

Cao Y, Slaney C Y, Bidwell B N, Parker B S, Johnstone C N, Rautela J, et al. *BMP4 inhibits breast cancer metastasis by blocking myeloid-derived suppressor cell activity*. Cancer research. 2014; 74(18):5091-102.

Chan C J, Martinet L, Gilfillan S, Souza-Fonseca-Guimaraes F, Chow M T, Town L, et al. *The receptors CD96 and CD226 oppose each other in the regulation of natural killer cell functions*. Nature immunology. 2014; 15(5): 431-8.

Demaria S, Volm M D, Shapiro R L, Yee H T, Oratz R, Formenti S C, et al. *Development of tumor-infiltrating lymphocytes in breast cancer after neoadjuvant paclitaxel chemotherapy*. Clinical cancer research. 2001; 7(10): 3025-30 de Kruijf E M, Sajet A, van Nes J G, Putter H, Smit V T, Eagle R A, et al. *NKG2D ligand tumor expression and association with clinical outcome in early breast cancer patients: an observational study*. BMC cancer. 2012; 12:24.

DeRisi, et al. (*Nature Genetics* 14:457-460 (1996)

DeWitt S H, et al. (1993) *Proc. Natl. Acad. Sci. USA,* 90:6909-6913

Eckhardt B L, Parker B S, van Laar R K, Restall C M, Natoli A L, Tavaria M D, et al. *Genomic analysis of a spontaneous model of breast cancer metastasis to bone reveals a role for the extracellular matrix. Molecular cancer research*: MCR. 2005; 3(1):1-13

Egleton (1997) "Bioavailability and transport of peptides and peptide drugs into the brain" *Peptides* 18:1431-1439

Fix (1996) *Pharm Res.* 13:1760-1764

Germer et al., *Genome Res.* 10:258-266 (2000)

Guo et al., *Nucleic Acids Res.* 22:5456-5465 (1994)

Heid et al., *Genome Res.* 6:986-994 (1996)

Jia Y, Xu L, Lin Q, Zhu M, Ding L, Wu K, et al. *Levels of lymphocyte subsets in peripheral blood prior treatment are associated with aggressive breast cancer phenotypes or subtypes*. Medical oncology. 2014; 31(6):981.

Ladoire S, Arnould L, Apetoh L, Coudert B, Martin F, Chauffert B, et al. *Pathologic complete response to neoadjuvant chemotherapy of breast carcinoma is associated with the disappearance of tumor-infiltrating foxp3+ regulatory T cells*. Clinical cancer research. 2008; 14(8):2413-20.

Ladoire S, Mignot G, Dabakuyo S, Arnould L, Apetoh L, Rebe C, et al. *In situ immune response after neoadjuvant chemotherapy for breast cancer predicts survival*. The Journal of pathology. 2011; 224(3):389-400

Langer (1990) *Science* 249:1527-1533

Maskos and Southern, *Nuc. Acids Res.* 20:1679-84, 1992

Moore et al., *BBA,* 1402:239-249, 1988;

Nagalla S, Chou J W, Willingham M C, Ruiz J, Vaughn J P, Dubey P, et al. *Interactions between immunity, proliferation and molecular subtype in breast cancer prognosis*. Genome biology. 2013; 14(4):R34

Neri S, Mariani E, Meneghetti A, Cattini L, Facchini A. *Calcein-acetyoxymethyl cytotoxicity assay: standardization of a method allowing additional analyses on recovered effector cells and supernatants.* Clin Diagn Lab Immunol. 2001; 8(6):1131-5

Patton (1998) *Biotechniques* 16:141-143

Pease et al., *Proc. Natl. Acad. Sci. USA* 91(11):5022-5026 (1994)

Putney (1998) *Nat. Biotechnol.* 16:153-157

Rouzier R, Perou C M, Symmans W F, Ibrahim N, Cristofanilli M, Anderson K, et al. *Breast cancer molecular subtypes respond differently to preoperative chemotherapy.* Clinical cancer research. 2005; 11(16):5678-85.

Samanen (1996) *J. Pharm. Pharmacol.* 48:119-135

Smith et al., *Science* 258:1122-1126 (1992)

Urdea et al., *Nucleic Acids Symp. Ser.,* 24:197-200 (1991)

Wedemeyer et al., *Clinical Chemistry* 48:9 1398-1405, 2002

Weissleder et al., *Nature Medicine* 6:351-355, 2000

Withana N P, Blum G, Sameni M, Slaney C, Anbalagan A, Olive M B, et al. *Cathepsin B inhibition limits bone metastasis in breast cancer.* Cancer research. 2012; 72(5): 1199-209

Yan M, Jene N, Byrne D, Millar E K, O'Toole S A, McNeil C M, et al. *Recruitment of regulatory T cells is correlated with hypoxia-induced CXCR4 expression, and is associated with poor prognosis in basal-like breast cancers.* Breast cancer research: BCR. 2011; 13(2):R47

---

---

The invention claimed is:

1. A method of treating a triple-negative breast neoplasm in a subject in need thereof, the method comprising:
   (a) screening the neoplasm for the expression of IRF9;
   (b) assessing the expression of IRF9 in the neoplasm relative to a control level; and
   (c) based on the assessment in step (b):
      (i) administering an effective amount of an agent that upregulates the level of Type I IFN to a subject assessed as having a lower of level of expression of IRF9 relative to the control level, or
      (ii) administering an effective amount of an agent selected anti-PD1, anti-PD-L1, a toxin which downregulates neoplastic cell proliferation, and combinations thereof to a subject assessed as having the same or higher level of expression of IRF9 relative to the control level.

2. The method according to claim 1 wherein said neoplasm is at risk of metastatic spread or has undergone metastatic spread.

3. The method according to claim 1 wherein said Type I IFN is IFN-α.

4. The method according to claim 1 wherein said Type I IFN is IFN-β.

5. The method according to claim 1 wherein said agent which upregulates the level of Type I IFN is selected from the group consisting of:
   (i) a Type I IFN protein or functional fragment thereof;
   (ii) a nucleic acid molecule encoding a Type I IFN or functional fragment thereof;
   (iii) a proteinaceous or non-proteinaceous molecule which upregulates the expression of a Type I IFN such as by modulating the transcriptional or translational regulation of a Type I IFN gene; and
   (iv) a proteinaceous or non-proteinaceous molecule which interacts with a Pattern Recognition receptor.

6. The method according to claim 5 wherein said proteinaceous or non-proteinaceous molecule which interacts with a Pattern Recognition receptor is a Toll-like receptor (TLR) agonist.

7. The method according to claim 6 wherein said Toll-like receptor agonist is selected from the group consisting of a TLR3 agonist, TLR7 agonist, TLR8 agonist and TLR9 agonist.

8. The method according to claim 7 wherein said TLR3 agonist is selected from the group consisting of polyI:C, polyA:U and PolyI:C:L:C.

9. The method according to claim 7 wherein said TLR9 agonist is CpG.

10. The method according to claim 6 wherein said TLR agonist is a TLR7/8 agonist.

11. The method according to claim 10 wherein said TLR7/8 agonist is imiquimod.

12. The method according to claim 1, wherein said toxin which downregulates neoplastic cell proliferation is selected from the group consisting of chemotherapy and radiotherapy.

13. The method according to claim 12 wherein said chemotherapy is selected from the group consisting of: Actinomycin D, Arsenic Trioxide, Asparaginase, Bleomycin, Busulfan, Carboplatin, Carmustine, Chlorambucil, Cisplatin, Corticosteroids, Cyclophosphamide, Daunorubicin, Docetaxel, Doxorubicin, Epirubicin, Etoposide, Fludarabine, Fluorouracil, Gemcitabine, Hydroxyurea, Idarubicin, Ifosfamide, Irinotecan, Lomustine, Melphalan, Mercaptopurine, Methotrexate, Mitomycin, Mitoxantrone, Oxaliplatin, Paclitaxel, Pemetrexed, Procarbizine, Raltitrexed, Streptozocin, Thioguanine, Thiotepa, Topotecan, Treosulfan, Vinblastine, Vincristine, Vindesine, and Vinorelbine.

14. The method according to claim 13 wherein said chemotherapy is doxorubicin.

15. The method according to claim 1 wherein said anti-PD1 or anti-PD-L1 is an antibody or functional fragment thereof.

16. The method according to claim 1 wherein said subject is human.

17. The method according to claim 1, wherein a subject administered an effective amount of an agent that upregulates the level of Type I IFN according to (c)(i), is further administered an effective amount of:
   anti-PD1 or anti-PD-L1;
   (ii) a toxin which downregulates neoplastic cell proliferation; or
   (iii) a combination of (i) and (ii).

18. The method according to claim 1 wherein the level of IRF9 expression is the level of IRF9 mRNA, cDNA or protein expression.

* * * * *